(12) United States Patent
Leban et al.

(10) Patent No.: US 7,531,517 B2
(45) Date of Patent: May 12, 2009

(54) INHIBITORS OF CANCER CELL, T-CELL AND KERATINOCYTE PROLIFERATION

(75) Inventors: Johann Leban, Martinsried (DE); Martin Kralik, Dornbirn (AT)

(73) Assignee: 4SC AG, Martinsried (DE)

( * ) Notice: Subject to any disclaimer, the term of this patent is extended or adjusted under 35 U.S.C. 154(b) by 18 days.

(21) Appl. No.: 11/501,722

(22) Filed: Aug. 10, 2006

(65) Prior Publication Data
US 2007/0037753 A1 Feb. 15, 2007

Related U.S. Application Data

(60) Provisional application No. 60/706,877, filed on Aug. 10, 2005.

(51) Int. Cl.
A61K 38/05 (2006.01)
(52) U.S. Cl. ...................................................... 514/19
(58) Field of Classification Search ........................ None
See application file for complete search history.

(56) References Cited

U.S. PATENT DOCUMENTS 5,492,895 A 2/1996 Vlasuk et al. .................. 514/18

FOREIGN PATENT DOCUMENTS

| EP | 0 543 310 A2 | 5/1993 |
|---|---|---|
| WO | WO 96/13266 | 5/1996 |
| WO | WO 2004/014882 | 2/2004 |
| WO | 2005/016859 A2 | 2/2005 |
| WO | WO 2005/016859 | 2/2005 |

OTHER PUBLICATIONS

McConnell et al., "Synthesis and 13C NMR Equilibria Studies of (1-13C)Leupeptin and Analogs" J. Org. Chem., 1998, 63, 5648-55.*
W. Liu, D.M., "Cysteine Protease Cathepsin S as a Key Step in Antigen Presentation", Spero; Drugs News Perspect., 17, 2004, 357-63.
Fehrentz J.A., "An Efficient Synthesis of Optically Active α-(t-Butoxycarbonylamino)-aldehydes from α-Amino Acids", CastroB. Synthesis, 676-678, 1983.
Linton et al, Acyl Dipeptides as Reversible Caspase Inhibitors, Part 2, Further Optimization, Bioorg. Med. Chem. Lett., (2002) vol. 12, No. 20, pp. 2973-2975.
Aubine et al, Retro Hydrazino-azapeptiods as Peptidomimetics of Proteasome Inhibitors, Journal of Medicinal Chemistry, (1995) vol. 48, No. 1, pp. 330-334.
Dodou et al, Synthesis of gossypol atropisomers and derivatives and evaluation of their anti-proliferative and anti-oxidant activity, Bioorg. Med. Chem., (1995) vol. 13, No. 13, pp. 4228 4237.
Bycroft et al, Synthesis of a Model relating to the Chromophores of Capreomycin and Viomycin, Tetrahedron Letters, (1969) vol. 30, pp. 2539-2541.
Herak et al, The Action of Hydrazines upon Thiazolidine-4-carboxylic-Acids I. Preparation of D-penicillamine from D-benzylpenilloic acid >>, Croatica Chemica Acta, (1977) Voo. 49, No. 1, pp. 141-148.
International Search Report dated Apr. 26, 2007.
Adams, J. et al, Proteasome inhibition: a new strategy in cancer treatment, Investigational New Drugs, (2000) vol. 18: pp. 109-121.
Groll, M. et al, Structure of 20S proteasome form yeast at 2.4A Resolution, Nature, (1997) vol. 386, pp. 463471.
Hee Lee, D. et al, Proteasome inhibitors: valuable new tools for cell biologists, Cell Biology, (1998), vol. 8, pp. 397-403.
Almond, J.B., et al. The Proteasome: A Novel Target for Cancer Therapy. Nature. (2002), vol. 16, pp. 433-443.
Weichold, F. et al. HIV-1 Protease Inhibitor Ritonavir Modulates Susceptibility to Apoptosis of Uninfected T Cells. Journal of Human Virology. (1999) vol. 2, No. 5, pp. 261-269.
Spaltenstein, A. et al. Design and Synthesis of Novel Protease Inhibitors. Tripeptide α', β'—Epoxyketones as Nanomolar Inactivators of the Proteasome. Tetrahedron Letters. (1996), vol. 37, No. 9, pp. 1343-1346.
Adams, J. et al, Potent and selective inhibitors of the proteasome: dipeptidyl boronic acids. Bioorganic & Medicinal Chemistry Letters. (1998), vol. 8, pp. 333-338.

(Continued)

Primary Examiner—Cecilia Tsang
Assistant Examiner—Christina Marchetti Bradley
(74) Attorney, Agent, or Firm—Baker, Donelson, Bearman, Caldwell & Berkowitz

(57) ABSTRACT

The invention relates to compounds of the general formula (I) and salts and physiologically functional derivatives thereof, (I)

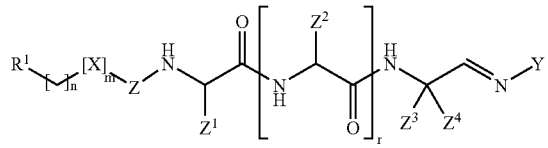

wherein
Y is —$NR^aR^b$, —$NR^cC=ONR^aR^b$, —$NR^cC=SNR^aR^b$, —$NR^cC=NR^dN^aR^b$, heterocycle, —$C=ONR^aR^b$, heterocycle, or aryl;
n is 0 to 8; m is 0, or 1; r is 0 to 3; t is 0 to 3;
X is O or N;
Z is $CH_2$, C=O, C=S or a single bond;
$Z^1$ is CO—$R^2$, CS—$R^2$, $(CH_2)_t$—$R^2$ or the side-chain of a naturally occuring amino acid;
$Z^2$ is CO—$R^2$, CS—$R^2$ or $(CH_2)_t$—$R^3$ or the side-chain of a naturally occuring amino acid;
$Z^3$ is CO—$R^2$, CS—$R^2$ or $(CH_2)_t$—$R^4$ or the side-chain of a naturally occuring amino acid;
$Z^4$ is H, alkyl, alkoxy, or cycloalkyl;
$R^1$, $R^2$, $R^3$, and $R^4$ are independently from each other H, OH, SH, $NH_2$, CN, $NO_2$, alkyl, cycloalkyl, heterocycloalkyl, haloalkyl, alkylthio, haloalkyloxy, hydroxyalkyl, hydroxyalkylamino, alkylamino, alkylaryl, alkylsulfinyl, alkylsulfonyl, alkylthioalkyl, alkylsulfinylalkyl, alkylsulfonylalkyl, alkoxyalkyl, alkoxy, aryloxy, heteroaryl, aryl, or halogen.

2 Claims, No Drawings

OTHER PUBLICATIONS

Flannery, T. et al. The Clinical Significance of Cathepsin S Expression in Human Astrocytomas. American Journal of Pathology. (2003), vol. 163, pp. 175-182.

McConnell et al. Synthesis and <13>C NMR equilibria Studies of (1-<13>C)leupeptin and Analogs. Journal of Organic Chemistry. (1998) vol. 63, No. 16, pp. 5648-5655.

Yasuda, Y. et al. The Role of Cathepsins in Osteoporosis and Arthritis: Rationale for the Design of New Therapeutics. Advanced Drug Delivery Reviews. (2004), vol. 57, pp. 973-993.

Nahm, S. et al. N-Methoxy-N-Methylamides As Effective Acylating Agents. Tetrahedron Letters. (1981), vol. 22, No. 39, pp. 3815-3818.

* cited by examiner

INHIBITORS OF CANCER CELL, T-CELL AND KERATINOCYTE PROLIFERATION

CROSS REFERENCE TO A RELATED APPLICATION

This application claims priority to U.S. Provisional Application No. 60/706,877 filed Aug. 10, 2005, the content of which is incorporated herein by reference in its entirety.

FIELD OF THE INVENTION

The present invention relates to compounds of the general formula (I) and/or (VI), or a salt or a physiologically functional derivative or a stereoisomer thereof, for use as a medicament. The compounds of the invention are useful for the treatment of diseases associated with abnormal and hyperproliferation of cells in a mammal, especially humans. In particular, they are useful for the treatment of cancer and of diseases characterized by the hyperproliferation of cells. Moreover, the substances of the invention are particularly useful for the treatment of diseases in which the inhibition of the proteasome, of cathepsins, especially cathepsin S, or of other proteases results in a beneficial effect, e.g. myocardial infarct, stroke and other reperfusion injuries, arthritis, osteoporosis, psoriasis and other inflammatory and autoimmune diseases. neurodermitis, psoriasis etc. Furthermore a process of preparing said compounds is disclosed.

BACKGROUND OF THE INVENTION

The proteasome plays an important role in the regulation of cellular functions being the central enzymatic activity in the ubiquitin-dependent degradation pathway for cellular proteins. The degradation of proteins responsible for processes like cell growth and division, cell differentiation, cell death, the up- and down-regulation of signaling pathways (e.g. NF-κB-pathway) and many other cellular activities is pivotal for the physiological functioning of cells. The human proteasome is a multifunctional protease consisting of three different catalytic activities, tryptic, chymotryptic and postglutamyl, harbored within a complex of 28 different subunits (20S proteasome) which are even part of a bigger proteolytic complex (26S proteasome) which also includes all kinds of associated proteins. D. H. Lee, A. L. Goldberg; Trends in Cell Biology, 8, 1998, 397-403. Groll M, Ditzel l, Lowe J, Stock D, Bochter M, Huber R; 1997, Nature, 386, 463-471. Adams, J.; Palobella, V. J.; Elloitt, P. J. Invest. New Drugs 2000, 18, 109. Allmond, J. B.; Cohen, G. M. Leukemia 2002, 16. 433. Weichhold F F, Bryant J L, Pati S, Barabitskaya, Gallo R C, and Reitz Jr., MS; J. of Human Virology, 2, 5, 1999, 261-269. Spaltenstein A.; Leban, J. J.; Huang, J. J.; Reinhardt, K. R.; Viveros, O. H.; Sigafoos, J.; Crouch, R. Tetrahedron Lett. 1996, 37, 1343. The proteasome plays also an important role in the immune response by processing proteins of invading organisms for display by MHC complexes on the surface of cells of the immune system. Proteolytic activity of the immune proteasome is different from that of the constitutive cellular proteasome due to the expression of alternative catalytically active subunits. There have been many drug discovery projects in the pharmaceutical industry with the goal to identify modulators of proteasome activity, however, until today only one substance (Velcade/Bortezomib) in the field of tumors has reached the market and is approved for the treatment of multiple myeloma. Other substances are currently in various phases of clinical development, however, most of these compounds are, like Velcade, agents which covalently modify the proteasome and this may be the reason for many of the side effects of these agents.

In WO 96/13266, boronic ester and acid compounds are disclosed which can be used to reduce the proteolytic activity in animal cells.

Similar compounds are described by Adams et al. (Bioorganic & Medicinal Chemistry Letters, 1998 (8), 333-338. "Potent and selective inhibitors of the proteasome: dipeptidyl boronic acids").

In WO2004/014882, peptidic compounds are described as proteasome inhibitors. Sandrine Aubin, Bénédicte Martin, Jean-Guy Delcros, Yannick Arlot-Bonnemains, and Michèle Baudy-Floc'h, Journal of medicinical chemistry, vol. 48, no. 1, 330-334 disclose a series of hydrazine-azapeptoids designed as proteasome inhibitor peptidomimetics having antiproliferative properties.

In WO2005/016859 a series of boronic acid compounds, boronic acids and compositions thereof that can modulate apoptosis such as by inhibition of proteasome activity is disclosed. Kalliopi Dodou, Rosaleen J. Anderson, W. John Lough, David A. P. Small, Michael D. Shelley and Paul W. Groundwater Bioorganic & Medicinal Chemistry, vol. 13, no. 13, 4228-4237 disclose a series of bis and half Schiff's bases and gossypol and tests showing their antiproliferative activity.

Human cysteine proteases of the papain family have been recognized as potential drug targets for the treatment of a number of diseases, eg. Musculoskeletal diseases, various inflammatory diseases, including rheumatoid arthritis, osteoporosis, artherosclerosis and autoimmune diseases (Y. Yasuda, J. Kaleta, D. Bromme; Adv Drug Deliv Rev., 57, 2005, 973-93). Cathepsin S, along with other lysosomal proteases, plays an important role in the major histocompatibility complex class II-restricted antigen presentation, especially in the degradation of the invariant chain, a chaperone peptide bound to the class II complex. (W. Liu, D. M. Spero; Drugs News Perspect., 17, 2004, 357-63.) Furthermore, the role of cathepsin S in propagation of cancer is under discussion, i.e. it has been shown that it is facilitating tumor cell invasion in astrocytomas (T. Flannery et al.; American Journal of Pathology, 163, 2003, 175-82).

The problem to be solved by the invention at hand is to provide alternative inhibitors of the proteasome, cathepsin S and other proteases.

Except for their activity in the treatment of cancer, compounds of the present invention can be used for the prevention or treatment in numerous diseases, especially reperfusion injuries (e.g. myocardial infarct, stroke, etc.) and diseases associated with the hyperproliferation of T-cells and/or keratinocytes, and also diseases caused by the uninhibited growth of invading organisms like bacteria and parasites.

Presently, only unsatisfactory therapies for the treatment of these diseases exist, which are often only partially effective or only effective in patient subpopulations. Moreover, existing therapies are frequently accompanied by severe adverse effects. There is, therefore, a necessity for new medicaments preferably without adverse effects for the therapy of these diseases.

The object of the present invention is solved by the subject-matter of the independent claims. Further advantageous features, aspects and details of the invention are evident from the dependent claims, the description, the figures, and the examples of the present application.

The present invention relates to compounds of the general Formulas (I) and/or (VI) or a salt or a stereoisomer thereof,

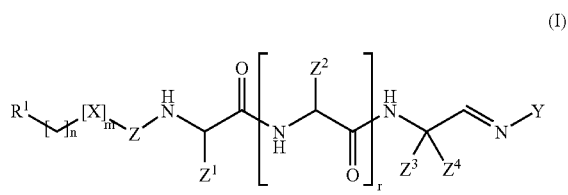

(I)

wherein
Y is —NR$^a$R$^b$, —NR$^c$C=ONR$^a$R$^b$, —NR$^c$C=SNR$^a$R$^b$, —NR$^c$C=NR$^d$N$^a$R$^b$, —C=ONR$^a$R$^b$, heterocycle, or aryl;

R$^a$, R$^b$, R$^c$, R$^d$ independently represents H, —CN, —OH, alkoxy, —SH, alkyl, alkenyl- or alkynylthio, —CO$_2$R$^{4'}$, —C(O)R$^{4'}$, —SO$_2$NR$^{4'}$, —SO$_2$-alkyl, -alkenyl or -alkynyl, —SO$_2$R$^{4'}$, SO$_3$R$^{4'}$, —NO$_2$, —NR$^{4'}$R$^{5'}$, alkyl-, alkenyl- or alkynyl amino, —N=CR$^{4'}$R$^{5'}$, —NR$^{4'}$C(O)R$^{4''}$, —NR$^{4'}$—CO-haloalkyl, -alkenyl or -alkynyl, —NR$^{4'}$—SO$_2$-haloalkyl, -alkenyl or -alkynyl, —NR$^{4'}$—SO$_2$-alkyl, -alkenyl or -alkynyl, —NR$^{4'}$—CO-alkyl, -alkenyl or -alkynyl, —NR$^{4'}$(CH$_2$)$_n$heterocycle, —C(NR$^{4''}$)NR$^{4'}$benzimidazolyl, —C(NR$^{4''}$)NR$^{4'}$benzothiazolyl, —C(NR$^{4''}$)NR$^{4'}$benzoxazolyl, alkyl, alkenyl or alkynyl, cycloalkyl, -alkenyl or -alkynyl, —O(CH$_2$)$_n$[O(CH$_2$)$_n$]$_r$OCH$_3$, hydroxyalkyl(alkenyl, alkynyl)amino, hydroxycycloalkyl, -alkenyl or -alkynyl, hydroxyalkyl, -alkenyl or -alkynyl amino, halogen, haloalkyl, -alkenyl or -alkynyl, haloalkyl, -alkenyl or -alkynyl oxy, aryl, arylalkyl, -alkenyl or -alkynyl or a heterocycle;

R$^{4'}$, R$^{4''}$, R$^{5'}$ independently are H, halogen, alkyl, alkenyl or alkynyl, —C(NR$^7$)NR$^{7'}$R$^8$, —(CH$_2$)$_n$aryl, —CH$_2$)$_n$NR$^7$R$^8$, —C(O)NR$^7$R$^8$, —N=CR$^7$R$^8$, —NR$^7$C(O)R$^8$, cycloalkyl, -alkenyl or -alkynyl, heterocycloalkyl, -alkenyl or -alkynyl, haloalkyl, -alkenyl or -alkynyl, hydroxyalkyl, -alkenyl or -alkynyl, hydroxyalkyl, -alkenyl or -alkynyl aminoalkyl, -alkenyl or -alkynyl, heteroaryl, alkyl-, alkenyl- or alkynylaryl, or aryl;

R$^7$, R$^{7'}$, R$^8$ independently are H, halogen, alkyl, -alkenyl or -alkynyl, cycloalkyl, -alkenyl or -alkynyl, heterocycloalkyl, -alkenyl or -alkynyl, haloalkyl, -alkenyl or -alkynyl, hydroxyalkyl, -alkenyl or -alkynyl, -alkenyl or -alkynyl amino, alkyl-, alkenyl- or alkynylamino, heteroaryl, alkylaryl, or aryl;

n is 0 to 8;
m is 0, or 1;
r is 0 to 3;
t is 0 to 3;
X is O or N;
Z is CH$_2$, C=O, C=S or a single bond;
Z$^1$, Z$^2$, Z$^3$ are independently from each other CO—R$^2$, CS—R$^2$, (CH$_2$)$_t$—R$^2$ or a side-chain of the naturally occurring amino acids, which are alanine, arginine, asparagine, asparatic acid, cysteine, glutamine, glutamic acid, glycine, histidine, isoleucine, leucine, lysine, methionine, phenylalanine, proline, serine, threonine, tryptophane, tyrosine, or valine, and in case of proline, Z$^1$, Z$^2$ or Z$^3$ respectively, the carbon atom to which it is attached, and the —NH group which is attached to said carbon atom are part of the ring system of the proline side-chain;

Z$^4$ is H, alkyl, alkenyl or alkynyl, alkoxy, or cycloalkyl, -alkenyl or -alkynyl;

R$^1$, R$^2$, R$^3$, R$^4$ are independently from each other H, OH, SH, NH$_2$, CN, NO$_2$, alkyl, alkenyl or alkynyl, cycloalkyl, -alkenyl or -alkynyl, heterocycloalkyl, -alkenyl or -alkynyl, haloalkyl, -alkenyl or -alkynyl, alkyl-, alkenyl- or alkynyl thio, haloalkyl (alkenyl, alkynyl) oxy, hydroxyalkyl, -alkenyl or -alkynyl, hydroxyalkyl (alkenyl, alkynyl) amino, alkyl-, alkenyl- or alkynyl amino, alkyl-, alkenyl- or alkynyl amino, alkyl-, alkenyl- or alkynylaryl, alkyl-, alkenyl- or alkynylsulfinyl, alkyl-, alkenyl- or alkynylsulfonyl, alkyl-, alkenyl- or alkynyl thioalkyl (alkenyl, alkynyl), alkyl-, alkenyl- or alkynyl sulfinylalkyl (alkenyl, alkynyl), alkyl-, alkenyl- or alkynyl sulfonylalkyl (alkenyl, alkynyl), alkoxyalkyl(alkenyl, alkynyl), alkoxy, aryloxy, heteroaryl, aryl, halogen or residues of the following formula wherein
W is N, CR$^e$;
R$^e$ is H, halogen, alkyl, -alkenyl or -alkynyl, cycloalkyl, -alkenyl or -alkynyl, heterocycloalkyl, -alkenyl or -alkynyl, haloalkyl, -alkenyl or -alkynyl, hydroxyalkyl, -alkenyl or -alkynyl, -alkenyl or -alkynyl amino, alkyl-, alkenyl- or alkynylamino, heteroaryl, alkylaryl, or aryl;
R$^6$, R$^{6'}$ is independently H, OH, SO$_3$H, CO$_2$H, N(CH$_3$)$_2$, OPO$_3$H;

an alkyl group, if not stated otherwise, denotes a linear or branched C$_1$-C$_6$-alkyl, preferably a linear or branched chain of one to six carbon atoms, alkenyl denotes a linear or branched C$_2$-C$_6$-alkenyl, preferably a linear or branched chain of one to six carbon atoms, and alkynyl denotes a linear or branched C$_2$-C$_6$-alkynyl group, preferably a linear or branched chain of one to six carbon atoms, which can be substituted by one or more substituents $R^9$; $R^9$ being defined as above;

$R^9$ independently represents H, —CN, —OH, alkoxy, —SH, alkyl, alkenyl- or alkynylthio, —$CO_2R^{4'}$, —$C(O)R^{4'}$, —$SO_2NR^{4'}$, —$SO_2$-alkyl, -alkenyl or -alkynyl, —$SO_2R^{4'}$, $SO_3R^{4'}$, —$NO_2$, —$NR^{4'}R^{5'}$, alkyl-, alkenyl- or alkynyl amino, —N=$CR^{4'}R^{5'}$, —$NR^{4'}C(O)R^{4''}$, —$NR^{4'}$—CO-haloalkyl, -alkenyl or -alkynyl, —$NR^{4'}$—$SO_2$-haloalkyl, -alkenyl or -alkynyl, —$NR^{4'}$—$SO_2$-alkyl, -alkenyl or -alkynyl, —$NR^{4'}$—CO-alkyl, -alkenyl or -alkynyl, —$NR^{4'}$ ($CH_2)_n$heterocycle, —$C(NR^{4''})NR^{4'}$benzimidazolyl, —$C(NR^{4''})NR^{4'}$benzothiazolyl, —$C(NR^{4''})$ $NR^{4'}$benzoxazolyl, alkyl, alkenyl or alkynyl, cycloalkyl, -alkenyl or -alkynyl, —$O(CH_2)_n[O(CH_2)_n]_rOCH_3$, hydroxyalkyl(alkenyl, alkynyl)amino, hydroxycycloalkyl, -alkenyl or -alkynyl, hydroxyalkyl, -alkenyl or -alkynyl amino, halogen, haloalkyl, -alkenyl or -alkynyl, haloalkyl, -alkenyl or -alkynyl oxy, aryl, arylalkyl, -alkenyl or -alkynyl or a heterocycle;

the $C_1$-$C_6$-alkyl, $C_2$-$C_6$-alkenyl and $C_2$-$C_6$-alkynyl residue may be selected from the group comprising —$CH_3$, —$C_2H_5$, —CH=$CH_2$, —C≡CH, —$C_3H_7$, —CH($CH_3)_2$, —$CH_2$—CH=$CH_2$, —C($CH_3$)=$CH_2$, —CH=CH—$CH_3$, —C≡C—$CH_3$, —$CH_2$—C≡CH, —$C_4H_9$, —$CH_2$—CH($CH_3)_2$, —CH($CH_3$)—$C_2H_5$, —C($CH_3)_3$, —$C_5H_{11}$, —$C_6H_{13}$, —C($R^9)_3$, —$C_2(R^9)_5$, —$CH_2$—C($R^9)_3$, —$C_3(R^9)_7$, —$C_2H_4$—C($R^9)_3$, —$C_2H_4$—CH=$CH_2$, —CH=CH—$C_2H_5$, —CH=C($CH_3)_2$, —$CH_2$—CH=CH—$CH_3$, —CH=CH—CH=$CH_2$, —$C_2H_4$—C≡CH, —C≡C—$C_2H_5$, —$CH_2$—C≡C—$CH_3$, —C≡C—CH=$CH_2$, —CH=CH—C≡CH, —C≡C—C≡CH, —$C_2H_4$—CH($CH_3)_2$, —CH($CH_3$)—$C_3H_7$, —$CH_2$—CH($CH_3$)—$C_2H_5$, —CH($CH_3$)—CH ($CH_3)_2$, —C($CH_3)_2$—$C_2H_5$, —$CH_2$—C($CH_3)_3$, —$C_3H_6$—CH=$CH_2$, —CH=CH—$C_3H_7$, —$C_2H_4$—CH=CH—$CH_3$, —$CH_2$—CH=CH—$C_2H_5$, —$CH_2$—CH=CH—CH=$CH_2$, —CH=CH—CH=CH—$CH_3$, —CH=CH—$CH_2$—CH=$CH_2$, —C($CH_3$)=CH—CH=$CH_2$, —CH=C($CH_3$)—CH=$CH_2$, —CH=CH—C($CH_3$)=$CH_2$, —$CH_2$—CH=C($CH_3)_2$, C($CH_3$)=C ($CH_3)_2$, —$C_3H_6$—C≡CH, —C≡C—$C_3H_7$, —$C_2H_4$—C≡C—$CH_3$, —$CH_2$—C≡C—$C_2H_5$, —$CH_2$—C≡C—CH=$CH_2$, —$CH_2$—CH=CH—C≡CH, —$CH_2$—C≡C—C≡CH, —C≡C—CH=CH—$CH_3$, —CH=CH—C≡C—$CH_3$, —C≡C—C≡C—$CH_3$, —C≡C—$CH_2$—CH=$CH_2$, —CH=CH—$CH_2$—C≡CH, —C≡C—$CH_2$—C≡CH, —C($CH_3$)=CH—CH=$CH_2$, —CH=C($CH_3$)—CH=$CH_2$, —CH=CH—C($CH_3$)=$CH_2$, —C($CH_3$)=CH—C≡CH, —CH=C ($CH_3$)—C≡CH, —C≡C—C($CH_3$)=$CH_2$, —$C_3H_6$—CH($CH_3)_2$, —$C_2H_4$—CH($CH_3$)—$C_2H_5$, —CH($CH_3$)—$C_4H_9$, —$CH_2$—CH($CH_3$)—$C_3H_7$, —CH($CH_3$)—$CH_2$—CH($CH_3)_2$, —CH($CH_3$)—CH($CH_3$)—$C_2H_5$, —$CH_2$—CH($CH_3$)—CH($CH_3)_2$, —$CH_2$—C($CH_3)_2$—$C_2H_5$, —C($CH_3)_2$—$C_3H_7$, —C($CH_3)_2$—CH($CH_3)_2$, —$C_2H_4$—C($CH_3)_3$, —CH($CH_3$)—C($CH_3)_3$, —$C_4H_8$—CH=$CH_2$, —CH=CH—$C_4H_9$, —$C_3H_6$—CH=CH—$CH_3$, —$CH_2$—CH=CH—$C_3H_7$, —$C_2H_4$—CH=CH—$C_2H_5$, —$CH_2$—C($CH_3$)=C($CH_3)_2$, —$C_2H_4$—CH=C($CH_3)_2$, —$C_4H_8$—C≡CH, —C≡C—$C_4H_9$, —$C_3H_6$—C≡C—$CH_3$, —$CH_2$—C≡C—$C_3H_7$, —$C_2H_4$—C≡C—$C_2H_5$;

a cycloalkyl group denotes a non-aromatic ring system containing three to eight carbon atoms, preferably four to eight carbon atoms, wherein one or more of the carbon atoms in the ring can be substituted by a group $R^9$ being as defined above; the $C_3$-$C_8$-cycloalkyl residue may be selected from the group comprising -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$, morpholine-4-yl, piperazinyl, 1-alkylpiperazine-4-yl;

the following definitions are given on the example of alkyl but also enclose alkenyl and alkynyl to be placed at the position of alkyl;

a heterocycloalkyl group denotes a non-aromatic ring system containing 2 to 10 carbon atoms and at least one heteroatom like O, N, or S, wherein one or more of the carbon atoms in the ring can be substituted by $R^9$; prefered heterocycloalkyl groups are cyclic amine, morpholine, cyclic urea, cyclic thiourea, cyclic guanidine, diketopiperazine, lactam and imidazolidine-2,4-dione;

an alkoxy group denotes an O-alkyl (alkenyl, alkynyl) group, the alkyl group being as defined above; the alkoxy group is preferably a methoxy, ethoxy, isopropoxy, t-butoxy or pentoxy group;

an alkylthio group denotes an S-alkyl group, the alkyl group being as defined above;

an alkylsulfinyl group denotes a —$S(O)R^f$ group, where $R^f$ is alkyl as defined above, e.g. methylsulfinyl, ethylsulfinyl, propylsulfinyl, butylsulfinyl (including all isomeric forms), and the like.

an alkylsulfonyl group denotes a —$S(O)_2R^f$ group, where $R^f$ is alkyl as defined above, e.g. methylsulfonyl, ethylsulfonyl, propylsulfonyl, butylsulfonyl (including all isomeric forms), and the like.

an alkylthioalkyl group denotes a -(alkylene)-$SR^f$ group, where $R^f$ is alkyl as defined above, e.g. methylthioethyl, ethylthiopropyl (including all isomeric forms), and the like.

an alkylsulfinylalkyl group denotes a -(alkylene)-$S(O)R^f$ group, where $R^f$ is alkyl as defined above, e.g. methylsulfinylethyl, ethylsulfinylpropyl (including all isomeric forms), and the like.

an alkylsulfonylalkyl group denotes a -(alkylene)-$S(O)_2R^f$ group, where $R^f$ is alkyl as defined above, e.g. methylsulfonylethyl, ethylsulfonylpropyl (including all isomeric forms), and the like.

an alkoxyalkyl group denotes a linear monovalent hydrocarbon group of one to six carbon atoms or a branched monovalent hydrocarbon group of three to six carbons substituted with at least one alkoxy group, preferably one or two alkoxy groups;

an haloalkyl group denotes an alkyl group which is substituted by one to five halogen atoms, the alkyl group being as defined above; the haloalkyl group is preferably a —$C(R')_3$, —$CR'(R'')_2$, —$CR'(R'')R'''$, —$C_2(R')_5$, —$CH_2$—$C(R')_3$, —$CH_2$—$CR'(R'')_2$, —$CH_2$—$CR'(R'')$ $R'''$, —$C_3(R')_7$, or —$C_2H_4$—$C(R')_3$, wherein R', R'', R''' represent F, Cl, Br or I, preferably F;

an hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —$OC(R')_3$, —$OCR'(R'')_2$, —$OCR'(R'')R'''$, —$OC_2$ $(R')_5$, —$OCH_2$—$C(R')_3$, —$OCH_2$—$CR'(R'')_2$, —$OCH_2$—$CR'(R'')R'''$, —$OC_3(R')_7$ or —$OC_2H_4$—$C(R')_3$, wherein R', R'', R''' represent F, Cl, Br or I, preferably F;

a hydroxyalkylamino group denotes an (HO-alkyl)$_2$—N— group or HO-alkyl-NH— group, the alkyl group being as defined above;

an alkylamino group denotes an HN-alkyl or N-dialkyl group, the alkyl group being as defined above;

a halogen group is fluorine, chlorine, bromine, or iodine;

an aryl group denotes an aromatic group having five to fifteen carbon atoms, which can be substituted by one or more substituents R⁹, wherein R⁹ being as defined above, preferably phenyl, 1-naphthyl, 2-naphthyl, biphenyl, 1-anthracenyl, or 2-anthracenyl;

a heteroaryl group denotes a 5- to 10-membered heterocyclic group which contains at least one heteroatom like O, N, S. This heterocyclic group can be fused to another ring. For example, this group can be selected from a thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thia-diazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, 1H-tetrazol-2-yl, 1H-tetrazol-3-yl, tetrazolyl, 2-indolyl, 3-indolyl, 2-indolinyl, 3-indolinyl, benzo[b]furanyl, benzo[b]thiophenyl, benzimidazolyl, benzothiazolyl, benzoxazolyl, quinazolinyl, quinoxazolinyl, 9H-thioxanthene-10,10-dioxide, quinolinyl, tetrahydroquinolinyl, isoquinolinyl, or tetrahydroisoquinolinyl group. This heterocyclic group can be substituted by one or more substituents R⁹, wherein R⁹ being as defined above;

a heterocycle denotes a heterocycloalkyl group or a heteroaryl group;

an alkylaryl or arylalkyl group denotes an alkyl group (see def. 'alkyl'), which is bound to an aryl fragment (see def. 'aryl') via a single bond. The linkage to the central moiety might occur via the alkyl part or the aryl part, preferably benzyl;

an aryloxy group denotes an aryl group (see def. 'aryl'), which is bound to the central moiety via a oxygen atom, preferably phenoxy.

Compounds of the present invention may exist as different optical isomers the nature of which will depend upon whether each modified amino acid residue is present in its "S" or "R" chiral form. The present invention includes within its scope each possible isomer. Preferred compounds of the present invention include those wherein all chiral centres are present in their "S" chiral form.

The invention also provides a pharmaceutical composition comprising a compound of Formulas (I) and/or (VI) in free form or in the form of pharmaceutically acceptable salts and physiologically functional derivatives, together with a pharmaceutically acceptable diluent or carrier thereof.

The term "physiologically functional derivative" as used herein refers to compounds which are not pharmaceutically active themselves but which are transformed into their pharmaceutical active form in vivo, i.e. in the subject to which the compound is administered. Examples of physiologically functional derivatives are prodrugs.

In addition, the present invention provides methods for preparing the compounds of the invention such as compounds of Formulas (I) and/or (VI).

The compounds of formula (I) may be obtained via various methods. e.g. compounds of formula (I) may be prepared starting from commercially available protected amino acids. Such compounds may be converted to their respective N,O-dimethylhydroxylamide derivatives by standard peptide coupling reagents (Nahm S., Weinreb S., Tet. Lett. 22, 3815-3818, 1981). The protected amino acid aldehyd can be obtained by reduction with lithium aluminium hydride (Fehrentz J. A., CastroB. Synthesis, 676-678, 1983 ). The protected amino acid aldehydes can be converted by standard conditions such as heating in ethanol water in the presence of sodium acetate and the appropriate amine, hydrazide semicarbazide, thiosemicarbazide, cyclic semicarbazides or aminoguanidines to yield the appropriate protected amino acid imine. These compounds can be converted by standard peptide deprotection and coupling reactions with commercially obtainable amino acids to compounds of the formula (I).

In a preferred embodiment of the invention, Y is a group of formula (II).

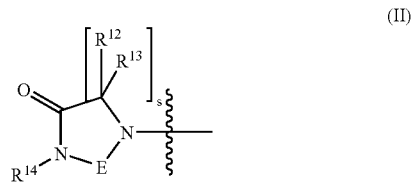

(II)

wherein
s is 1 to 3;
R¹², R¹³ are independently H, or alkyl;
R¹⁴ is H, alkyl, SO₃H, or R¹;
E is CH₂, CO, or CS;
Z is CO; X is O; t=1, r=1, m=1, n=1,
Z¹ is (CH₂)$_t$—R²; Z² is (CH₂)$_r$—R³; Z³ is (CH₂)$_t$—R⁴; Z⁴ is H, or methyl;
R², R³, R⁴ are independently from each other H, Phenyl, Benzyl, 3-Benzothienyl, 2-Thienyl, 2-Thiazolyl, 4-Pyridyl, 3-Pyridyl, 2-Pyridyl, 2-Quinolyl, 2-Indolyl, 3-Indolyl, Ethylbenzene, 2-Naphtyl, 1-Naphtyl, p-Aminobenzyl, p-Azidobenzyl, p-Bromobenzyl, p-Hydroxy, p-tButyl-benzyl, p-Carboxybenzyl, p-Chloro-benzyl, p-Cyanobenzyl, 3,4-Dichlorobenzyl, p-Fluorobenzyl, p-Iodobenzyl, p-Nitrobenzyl, Pentafluorobenzyl, p-Phenylbenzyl, m-Fluorobenzyl, p-Methyl-benzyl, Tryptoline-3-carboxylic acid, 5-Methyl-tryptophan, 4-Methyl-tryptophan, 3-Methyl-1H-indolyl, 2-Methyl-1H-indolyl, 2-Amino-4-ethyl-phenol, 2,6-Dibromo-4-ethyl-phenol, 4-Ethyl-2,6-diiodo-phenol, 1-Ethoxy-4-ethyl-benzene, 1-Ethyl-4-methoxy-benzene, 4-Ethyl-2-iodo-phenol, (4-Ethyl-phenyl)-phenyl-methanone, 1-Thiophen-2-yl-ethanol, 1,2,3,4-Tetrahydro-isoquinoline-3-carboxylic acid, 7-Hydroxy-1,2,3,4-tetrahydro-isoquinoline-3-carboxylic acid, Sulfuric acid mono-(4-ethyl-phenyl) ester, Phosphoric acid mono-(4-ethyl-phenyl) ester, 4-Ethyl-2-nitro-phenol, 1-tert-Butoxy-4-ethyl-benzene and 4-(4-Ethyl-phenoxy)-phenol;
R¹ is phenyl, 4-pyridyl, 3-pyridyl, 2-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, 2-indolyl, 3-indolyl, 1-imidazolyl, 2-imidazolyl, 4-tetrahydro-thieno[3,4-d]imidazol-2-one-yl, 4-phenoxy-benz-1-yl, which are optionally substituted by halogen, alkoxy, haloalkyl, or haloalkoxy.

In another embodiment of the invention, Y is a group of formula (II),
Z is CO, t=1, r=1, m=0, n=4,
Z¹ is (CH₂)$_t$—R²; Z² is (CH₂)$_r$—R³; Z³ is (CH₂)$_t$—R⁴; Z⁴ is H, or methyl;
R², R³, R⁴ are as defined above for formula (II), and R¹ is as defined above for formula (II).

In a more preferred embodiment of the invention, Y is a group of formula (II),
s is 1; R¹⁴ is H, or methyl; E is CH₂; R¹², R¹³ are independently H, or methyl;

Z is CO, X is O, t=1, r=1, m=1, n=1,
Z$^1$ is (CH$_2$)$_t$—R$^2$; Z$^2$ is (CH$_2$)$_t$—R$^3$; Z$^3$ is (CH$_2$)$_t$—R$^4$; Z$^4$ is H, or methyl;
R$^2$, R$^3$, R$^4$ are as defined above for formula (II);
and R$^1$ is as defined above for formula (II).

In a more preferred embodiment of the invention, Y is a group of formula (II),
s is 1; R$^{14}$ is H, or methyl; E is CH$_2$; R$^{12}$, R$^{13}$ are independently H, or methyl;
Z is CO, t=1, r=1, m=0, n=4,
Z$^1$ is (CH$_2$)$_t$—R$^2$; Z$^2$ is (CH$_2$)$_t$—R$^3$; Z$^3$ is (CH$_2$)$_t$—R$^4$; Z$^4$ is H, or methyl;
R$^2$, R$^3$, R$^4$ are as defined above for formula (II);
and R$^1$ is as defined above for formula (II).

In another embodiment of the invention, Y is an hydantoin residue, as exemplified in formula (III)

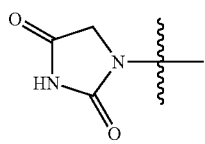

(III)

Z is CO, X is O, t=1, r=1, m=1, n=1,
Z$^1$ is (CH$_2$)$_t$—R$^2$; Z$^2$ is (CH$_2$)$_t$—R$^3$; Z$^3$ is (CH$_2$)$_t$—R$^4$; Z$^4$ is H, or methyl;
R$^2$, R$^3$, R$^4$ are as defined above for formula (II);
and R$^1$ is as defined above for formula (II).

In another embodiment of the invention, Y is a group of formula (III),
Z is CO, t=1, r=1, m=0, n=4,
Z$^1$ is (CH$_2$)$_t$—R$^2$; Z$^2$ is (CH$_2$)$_t$—R$^3$; Z$^3$ is (CH$_2$)$_t$—R$^4$; Z$^4$ is H, or methyl;
R$^2$, R$^3$, R$^4$ are as defined above for formula (II);
and R$^1$ is as defined above for formula (II).

In another embodiment of the invention, Y is a group of formula (III),
Z is CO, t=1, r=1, m=0, n=4,
Z$^1$ is (CH$_2$)$_t$—R$^2$; Z$^2$ is (CH$_2$)$_t$—R$^3$; Z$^3$ is (CH$_2$)$_t$—R$^4$; Z$^4$ is H, or methyl;
R$^2$, R$^3$, R$^4$ are independently of each other H, benzyl, or indolyl optionally substituted by halogen; and R$^1$ is as defined above for formula (II).

In another embodiment of the invention, Y is a group of formula (III),
Z is CO, X is O, t=1, r=1, m=1, n=1,
Z$^1$ is (CH$_2$)$_t$—R$^2$; Z$^2$ is (CH$_2$)$_t$—R$^3$; Z$^3$ is (CH$_2$)$_t$—R$^4$; Z$^4$ is H, or methyl;
R$^2$, R$^3$, R$^4$ are independently of each other H, benzyl, or indolyl optionally substituted by halogen; and R$^1$ is as defined above for formula (II).

In another preferred embodiment of the invention, Y is a group of formula (IV).

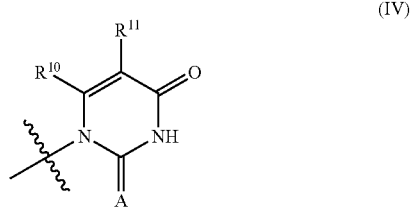

(IV)

wherein
R$^{10}$, R$^{11}$ are independently H, alkyl, alkoxy, halogen, haloalkyl, haloalkoxy;
A is O, S, or NR$^{4'}$;
Z is CO, X is O, t=1, r=1, m=1, n=1,
Z$^1$ is (CH$_2$)$_t$—R$^2$; Z$^2$ is (CH$_2$)$_t$—R$^3$; Z$^3$ is (CH$_2$)$_t$—R$^4$; Z$^4$ is H, or methyl;
R$^2$, R$^3$, R$^4$ are as defined above for formula (II);
and R$^1$ is as defined above for formula (II).

In another embodiment of the invention, Y is a group of formula (IV),
Z is CO, t=1, r=1, m=0, n=4,
Z$^1$ is (CH$_2$)$_t$—R$^2$; Z$^2$ is (CH$_2$)$_t$—R$^3$; Z$^3$ is (CH$_2$)$_t$—R$^4$; Z$^4$ is H, or methyl;
R$^2$, R$^3$, R$^4$ are independently of each other H, benzyl, or indolyl optionally substituted by halogen; and R$^1$ is as defined above for formula (II).

In another embodiment of the invention, Y is a group of formula (IV),
Z is CO, X is O, t=1, r=1, m=1, n=1,
Z$^1$ is (CH$_2$)$_t$—R$^2$; Z$^2$ is (CH$_2$)$_t$—R$^3$; Z$^3$ is (CH$_2$)$_t$—R$^4$; Z$^4$ is H, or methyl;
R$^2$, R$^3$, R$^4$ are independently of each other H, benzyl, or indolyl optionally substituted by halogen; and R$^1$ is as defined above for formula (II).

In another preferred embodiment of the invention, Y is a group of formula (IV),
R$^{10}$, R$^{11}$ are independently H, methyl, OCH$_3$, OC$_2$H$_5$, F, or CF$_3$; A is O,
Z is CO, X is O, t=1, r=1, m=1, n=1,
Z$^1$ is (CH$_2$)$_t$—R$^2$; Z$^2$ is (CH$_2$)$_t$—R$^3$; Z$^3$ is (CH$_2$)$_t$—R$^4$; Z$^4$ is H, or methyl;
R$^2$, R$^3$, R$^4$ are independently of each other H, benzyl, or indolyl optionally substituted by halogen; and R$^1$ is as defined above for formula (II).

In another preferred embodiment of the invention, Y is a group of formula (IV),
R$^{10}$, R$^{11}$ are independently H, methyl, OCH$_3$, OC$_2$H$_5$, F, or CF$_3$, A is O,
Z is CO, t=1, r=1, m=0, n=4,
Z$^1$ is (CH$_2$)$_t$—R$^2$; Z$^2$ is (CH$_2$)$_t$—R$^3$; Z$^3$ is (CH$_2$)$_t$—R$^4$; Z$^4$ is H, or methyl;
R$^2$, R$^3$, R$^4$ are independently of each other H, benzyl, or indolyl optionally substituted by halogen; and R$^1$ is as defined above for formula (II).

In another preferred embodiment of the invention, Y is a group of formula (IV),
R$^{10}$, R$^{11}$ are independently H, methyl, OCH$_3$, OC$_2$H$_5$, F, or CF$_3$; A is O,
Z is CO, X is O, t=1, r=1, m=1, n=1,
Z$^1$ is (CH$_2$)$_t$—R$^2$; Z$^2$ is (CH$_2$)$_t$—R$^3$; Z$^3$ is (CH$_2$)$_t$—R$^4$; Z$^4$ is H, or methyl; R$^2$, R$^3$, R$^4$ are independently of each other H, benzyl, or indolyl optionally substituted by halogen; and R¹ is as defined above for formula (II).

In another preferred embodiment of the invention, Y is a group of formula (IV), $R^{10}$, $R^{11}$ are independently H, methyl, $OCH_3$, $OC_2H_5$, F, or $CF_3$; A is O, Z is CO, t=1, r=1, m=0, n=4, $Z^1$ is $(CH_2)_r$—$R^2$; $Z^2$ is $(CH_2)_r$—$R^3$; $Z^3$ is $(CH_2)_r$—$R^4$; $Z^4$ is H, or methyl;

$R^2$, $R^3$, $R^4$ are independently of each other H, benzyl, or indolyl optionally substituted by halogen; and $R^1$ is as defined above for formula (II).

Another preferred embodiment of the invention are compounds according to the general formula V:

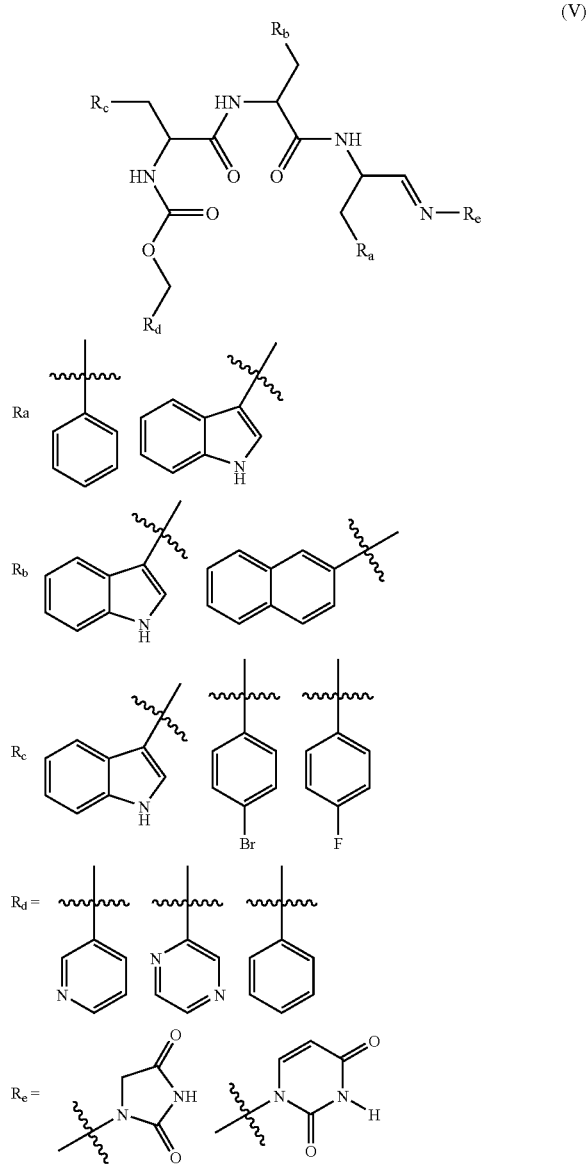

Wherein $R_a$, $R_b$, $R_c$, $R_d$ and $R_e$ are independent from each other selected as defined above.

The invention relates further to compounds according to formula (VI) or a salt or a stereoisomer thereof,

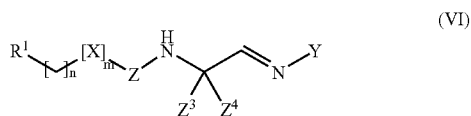

wherein

Y is —$NR^aR^b$, —$NR^cC$=$ONR^aR^b$, —$NR^cC$=$SNR^aR^b$, —$NR^cC$=$NR^dN^aR^b$, —C=$ONR^aR^b$, heterocycle, or aryl;

$R^a$, $R^b$, $R^c$, $R^d$ independently represents H, —CN, —OH, alkoxy, —SH, alkylthio, —$CO_2R^{4'}$, —$C(O)R^{4'}$, —$SO_2NR^{4'}$, —$SO_2$-alkyl, —$SO_2R^{4'}$, $SO_3R^{4'}$, —$NO_2$, —$NR^{4'}R^{5'}$, alkylamino, —N=$CR^{4'}R^{5'}$, —$NR^{4'}C(O)R^{4''}$, —$NR^{4'}$—CO-haloalkyl, —$NR^{4'}$—$SO_2$-haloalkyl, —$NR^{4'}$—$SO_2$-alkyl, —$NR^{4'}$—CO-alkyl, —$NR^{4'}(CH_2)_n$ heterocycle, —$C(NR^{4''})NR^{4'}$benzimidazolyl, —$C(NR^{4''})NR^{4'}$benzothiazolyl, —$C(NR^{4''})NR^{4'}$benzoxazolyl, alkyl, cycloalkyl, —$O(CH_2)_n[O(CH_2)_n]_rOCH_3$, hydroxyalkyl, hydroxycycloalkyl, hydroxyalkylamino, halogen, haloalkyl, haloalkyloxy, aryl, arylalkyl or a heterocycle;

$R^{4'}$, $R^{4''}$, $R^{5'}$ independently are H, halogen, alkyl, alkenyl, alkynyl, —$C(NR^7)NR^{7'}R^8$, —$(CH_2)_n$aryl, —$CH_2)_n$ $NR^7R^8$, —$C(O)NR^7R^8$, —N=$CR^7R^8$, —$NR^7C(O)R^8$, cycloalkyl, -alkenyl or -alkynyl, heterocycloalkyl, -alkenyl or -alkynyl, haloalkyl, -alkenyl or -alkynyl, hydroxyalkyl, -alkenyl or -alkynyl, hydroxyalkyl (alkenyl or -alkynyl) amino, alkyl-, alkenyl- or alkynyl amino, heteroaryl, alkyl-, alkenyl- or alkynyl aryl, or aryl;

$R^7$, $R^{7'}$, $R^8$ independently are H, halogen, alkyl, alkenyl, alkynyl, cycloalkyl, -alkenyl or -alkynyl, heterocycloalkyl, -alkenyl or -alkynyl, haloalkyl, -alkenyl or -alkynyl, hydroxyalkyl, -alkenyl or -alkynyl, hydroxyalkyl (-alkenyl or -alkynyl) amino, alkyl-, alkenyl- or alkynyl amino, heteroaryl, alkyl-, alkenyl- or alkynyl aryl, or aryl;

n is 0 to 8;

m is 0, or 1;

X is O or N;

Z is H, $CH_2$, C=O, C=S or a single bond;

$Z^3$ is CO—$R^2$, CS—$R^2$, $(CH_2)_r$—$R^2$ or a side-chain of the naturally occuring amino acids, which are alanine, arginine, asparagine, aspartic acid, cysteine, glutamine, glutamic acid, glycine, histidine, isoleucine, leucine, lysine, methionine, phenylalanine, proline, serine, threonine, tryptophane, tyrosine, or valine, and in case of proline, $Z^1$, $Z^2$ or $Z^3$ respectively, the carbon atom to which it is attached, and the —NH group which is attached to said carbon atom are part of the ring system of the proline side-chain;

$Z^4$ is H, alkyl, alkenyl, alkynyl, alkoxy, or cycloalkyl;

$R^1$ and $R^{1'}$ independently are H, OH, SH, $NH_2$, CN, $NO_2$, alkyl, alkenyl or alkynyl, cycloalkyl, -alkenyl or -alkynyl, heterocycloalkyl, -alkenyl or -alkynyl, haloalkyl, -alkenyl or -alkynyl, alkyl-, alkenyl- or alkynyl thio, haloalkyl (alkenyl, alkynyl) oxy, hydroxyalkyl, -alkenyl or -alkynyl, hydroxyalkyl (alkenyl, alkynyl) amino, alkyl-, alkenyl- or alkynyl amino, alkyl-, alkenyl- or alkynylaryl, alkyl-, alkenyl- or alkynylsulfinyl, alkyl-, alkenyl- or alkynylsulfonyl, alkyl-, alkenyl- or alkynyl thioalkyl (alkenyl, alkynyl), alkyl-, alkenyl- or alkynyl sulfinylalkyl(alkenyl, alkynyl), alkyl-, alkenyl- or alkynyl sulfonylalkyl (alkenyl, alkynyl), alkoxyalkyl(alkenyl, alkynyl), alkoxy, aryloxy, heteroaryl, aryl, halogen or a residue of the following formula

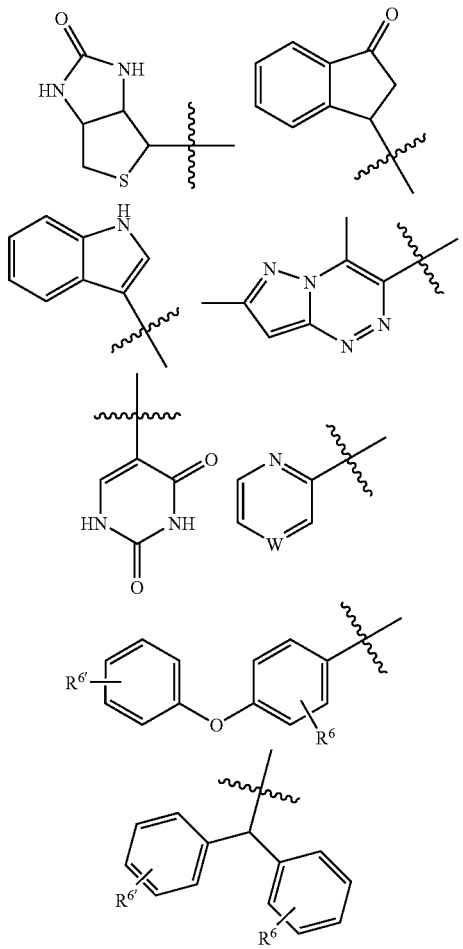

wherein

W is N, $CR^e$;

$R^e$ is H, halogen, alkyl, cycloalkyl, heterocycloalkyl, haloalkyl, hydroxyalkyl, hydroxyalkylamino, alkylamino, heteroaryl, alkylaryl, or aryl;

$R^6$, $R^{6'}$ is independently H, OH, $SO_3H$, $CO_2H$, $N(CH_3)_2$, $OPO_3H$;

The compounds of the Formulas (I) and/or (VI) to be used according to the invention can form salts with inorganic or organic acids or bases. Examples of pharmaceutically acceptable salts comprise without limitation non-toxic inorganic or organic salts such as acetate derived from acetic acid, aconitate derived from aconitic acid, ascorbate derived from ascorbic acid, benzoate derived from benzoic acid, cinnamate derived from cinnamic acid, citrate derived from citric acid, embonate derived from embonic acid, enantate derived from heptanoic acid, formiate derived from formic acid, fumarate derived from fumaric acid, glutamate derived from glutamic acid, glycolate derived from glycolic acid, chloride derived from hydrochloric acid, bromide derived from hydrobromic acid, lactate derived from lactic acid, maleate derived from maleic acid, malonate derived from malonic acid, mandelate derived from mandelic acid, methanesulfonate derived from methanesulfonic acid, naphthaline-2-sulfonate derived from naphthaline-2-sulfonic acid, nitrate derived from nitric acid, perchlorate derived from perchloric acid, phosphate derived from phosphoric acid, phthalate derived from phthalic acid, salicylate derived from salicylic acid, sorbate derived from sorbic acid, stearate derived from stearic acid, succinate derived from succinic acid, sulphate derived from sulphuric acid, tartrate derived from tartaric acid, toluene-p-sulfate derived from p-toluene-sulfonic acid and others. Such salts can be produced by methods known to someone of skill in the art and described in the prior art.

Other salts like oxalate derived from oxalic acid, which is not considered as pharmaceutically acceptable can be appropriate as intermediates for the production of compounds of the Formulas (I) and/or (VI) or a pharmaceutically acceptable salt thereof or stereoisomer thereof.

Thus, in one embodiment, the invention relates to the use of the compounds of the Formulas (I) and/or (VI) or a pharmaceutically acceptable salt or stereoisomer thereof if desired with appropriate adjuvants and additives for the production of a medicament for the treatment or prevention of tumors and cancer.

In a preferred embodiment the diseases and conditions for which the compounds of the present invention may be used include but are not limited to cancer as hematological (e.g. leukemia, lymphoma, myeloma and others) or solid tumors (for example breast, prostate, liver, bladder, lung, esophageal, stomach, colorectal, genitourinary, gastrointestinal, skin, pancreatic, brain, uterine, colon, head and neck, cervical, and ovarian, melanoma, astrocytoma, small cell lung cancer, non-small cell lung cancer, glioma, basal and squameous cell carcinoma, sarcomas as Kaposi's sarcoma, osteosarcoma and others).

In another embodiment, the invention relates to the use of the compounds of the Formulas (I) and/or (VI) or a pharmaceutically acceptable salt or stereoisomer thereof if desired with appropriate adjuvants and additives for the production of a medicament for the treatment or prevention of a disease characterized by hyperproliferation of keratinocytes and/or T cells.

Furthermore, the invention relates to a method of treatment or prevention of diseases which comprises the administration of an effective amount of compounds of the Formulas (I) and/or (VI) or a pharmaceutically acceptable salt or stereoisomer thereof.

In another preferred embodiment, the invention relates to the use of compounds of the Formulas (I) and/or (VI) or a pharmaceutically acceptable salt or stereoisomer thereof if desired with appropriate adjuvants and additives for the production of a medicament for the treatment or prevention of skin diseases in which a hyperproliferation of keratinocytes plays a role, especially preferably the skin diseases are selected from the group consisting of psoriasis, atopic dermatitis, actinic keratoses, hyperkeratoses like epidermolytic hyperkeratosis, Hyperkeratosis Lenticularis Perstans, Keratosis pilaris and Ichthyoses.

"Treatment" according to the present invention is intended to mean complete or partial healing of a disease, or alleviation of a disease or stop of progression of a given disease.

Furthermore, the invention relates to a method of treatment or prevention of diseases which comprises the administration of an effective amount of compounds of the formula (I) or a pharmaceutically acceptable salt or stereoisomer thereof. In a preferred embodiment, the diseases are characterized by hyperproliferation of keratinocytes and/or T cells, especially inflammatory disorders and immune disorders, preferably selected from the group consisting of Addison's disease, alopecia areata, Ankylosing spondylitis, haemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, auto-immune hemolysis, Bechet's disease, Boeck's disease, inflammatory bowel disease, Burkitt's lymphoma, Crohn's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, autoimmune demyelinating diseases, Dupuytren's contracture, encephalomyelitis, encephalomyelitis allergica, endophthalmia phacoanaphylactica, enteritis allergica, autoimmune enteropathy syndrome, erythema nodosum leprosum, idiopathic facial paralysis, chronic fatigue syndrome, febris rheumatica, glomerulo nephritis, Goodpasture's syndrome, Graves' disease, Hamman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgarls, polyarteritis nodosa, polyarthritis chronica primaria, polymyositis, polyradiculitis acuta, psoriasis, purpura, pyoderma gangrenosum, Quervain's thyreoiditis, Reiter's syndrome, sarcoidosis, ataxic sclerosis, progressive systemic sclerosis, scieritis, sclerodermia, multiple sclerosis, sclerosis disseminata, acquired spenic atrophy, infertility due to antispermatozoan antobodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphoma, parasitic diseases such as Leishmania, and immunesuppressed disease states such as viral infections following allograft transplantations, AIDS, cancer, chronic active hepatitis diabetes, toxic chock syndrome and food poisoning.

In a more preferred embodiment, the diseases are skin diseases in which T cells play a role, preferrably the diseases are selected from the group consisting of psoriasis, atopic dermatitis, alopecia areata, alopecia totalis, alopecia subtotalis, alopecia universalis, alopecia diffusa, lupus erythematodes of the skin, lichen planus, dermatomyostis of the skin, atopic eczema, morphea, sklerodermia, psoriasis vulgaris, psoriasis capitis, psoriasis guttata, psoriasis inversa, alopecia areata ophiasis-type, androgenetic alopecia, allergic contact eczema, irritative contact eczema, contact eczema, pemphigus vulgaris, pemphigus foliaceus, pemphigus vegetans, scarring mucosal pemphigoid, bullous pemphgoid, mucous pemphigoid, dermatitis, dermatitis herpetiformis duhring, urticaria, necrobiosis lipoidica, erythema nodosum, lichen vidal, prurigo simplex, prurigo nodularis, prurigo acuta, linear IgA dermatosis, polymorphic light dermatoses, erythema solaris, lichen sclerosus et atrophicans, exanthema of the skin, drug exanthema, purpura chronica progressiva, dihidrotic ekzema, Ekzema, fixed drug exanthema, photoallergic skin reaction, lichen simplex eriorale, dermatitis and "Graft versus Host-Disease", acne, rosacea, scarring, keloids and vitiligo.

In an even more preferred embodiment, the disease is a skin disease in which a hyperproliferation of keratinocytes plays a role. Especially preferred diseases are Psoriasis, atopic dermatitis, actinic keratoses, hyperkeratoses like epidermolytic hyperkeratosis, Hyperkeratosis Lenticularis Perstans, Keratosis pilaris and Ichthyoses.

The compounds according to the invention and medicaments prepared therewith are generally useful for the treatment of cell proliferation disorders, for the treatment or prophylaxis, immunological diseases and conditions (as for instance inflammatory diseases, neuroimmunological diseases, autoimmune diseases or other).

The compounds of the present invention can further be used for diseases that are caused by protozoal infestations in humans and animals. Such veterinary and human pathogenic protozoas are preferably intracellular active parasites of the phylum Apicomplexa or Sarcomastigophora, especially Trypanosoma, Plasmodia, Leishmania, Babesia and Theileria, Cryptosporidia, Sacrocystida, Amoebia, Coccidia and Trichomonadia. These active substances or corresponding drugs are especially suitable for the treatment of Malaria tropica, caused by *Plasmodiumn falciparum*, Malaria tertiana, caused by *Plasmodium vivax* or *Plasmodium ovale* and for the treatment of Malaria quartana, caused by *Plasmodium malariae*. They are also suitable for the treatment of Toxoplasmosis, caused by *Toxoplasma gondii*, Coccidiosis, caused for instance by *Isospora belli*, intestinal Sarcosporidiosis, caused by *Sarcocystis suihominis*, dysentery caused by *Entamoeba histolytica*, Cryptosporidiosis, caused by *Cryptosporidium parvum*, Chargas disease, caused by *Trypanosoma cruzi*, sleeping sickness, caused by *Trypanosoma brucei rhodesiense* or *gambiense*, the cutaneous and visceral as well as other forms of Leishmaniosis. They are also suitable for the treatment of animals infected by veterinary pathogenic protozoa, like *Theileria parva*, the pathogen causing bovine East coast fever, *Trypanosoma congolense congolense* or *Trypanosoma vivax vivax, Trypanosoma brucei brucei*, pathogens causing Nagana cattle disease in Africa, *Trypanosoma brucei evansi* causing Surra, *Babesia bigemina*, the pathogen causing Texas fever in cattle and buffalos, *Babesia bovis*, the pathogen causing European bovine Babesiosis as well as Babesiosis in dogs, cats and sheep, *Sarcocystis ovicanis* and *ovifelis* pathogens causing Sarcocystiosis in sheep, cattle and pigs, Cryptosporidia, pathogens causing Cryptosporidioses in cattle and birds, Eimeria and Isospora species, pathogens causing Coccidiosis in rabbits, cattle, sheep, goats, pigs and birds, especially in chickens and turkeys. The use of the compounds of the present invention is preferred in particular for the treatment of Coccidiosis or Malaria infections, or for the preparation of a drug or feed stuff for the treatment of these diseases. This treatment can be prophylactic or curative. In the treatment of malaria, the compounds of the present invention may be combined with other anti-malaria agents.

The compounds of the present invention can further be used for the prophylaxis and/or treatment of infectious diseases caused among others by bacteria and viruses, including opportunistic infections in a mammal, including a human. Said method comprises administering to the mammal an amount of at least one compound of the general Formulas (I) and/or (VI) and/or pharmaceutically acceptable salts thereof, effective to prevent and/or treat said infectious disease and/or opportunistic infection.

The compounds of Formulas (I) and/or (VI) and their pharmacologically acceptable salts can be administered to animals, preferably to mammals, and in particular to humans, as therapeutics per se, as mixtures with one another or in the form of pharmaceutical preparations which allow enteral or parenteral use and which as active constituent contain an effective dose of at least one compound of the Formulas (I) and/or (VI) or a salt thereof, in addition to customary pharmaceutically innocuous excipients and additives. The compounds of Formulas (I) and/or (VI) can also be administered in form of their salts, which are obtainable by reacting the respective compounds with physiologically acceptable acids and bases.

The production of medicaments containing the compounds of Formulas (I) and/or (VI) according to the invention and their application can be performed according to well-known pharmaceutical methods.

While the compounds of Formulas (I) and/or (VI) according to the invention for use in therapy may be administered in the form of the raw chemical compound, it is preferred to introduce the active ingredient, optionally in the form of a physiologically acceptable salt in a pharmaceutical composition together with one or more adjuvants, excipients, carriers, buffers, diluents, and/or other customary pharmaceutical auxiliaries. Such salts of the compounds may be anhydrous or solvated.

In a preferred embodiment, the invention provides medicaments comprising compounds of Formulas (I) and/or (VI) according to the invention, or a pharmaceutically acceptable salt or stereoisomer thereof, together with one or more pharmaceutically acceptable carriers thereof, and, optionally, other therapeutic and/or prophylactic ingredients. The carrier(s) must be "acceptable" in the sense of being compatible with the other ingredients of the formulation and not harmful to the recipient thereof.

A medicament of the invention may be those suitable for oral, rectal, bronchial, nasal, topical, buccal, sub-lingual, transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The compounds according to the invention, together with a conventional adjuvant, carrier, or diluent, may thus be placed into the form of medicament and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such Medicament and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compound useable according to the invention can be administered in a wide variety of oral and parenteral dosage forms. It will be obvious to those skilled in the art that the following dosage forms may comprise, as the active component, either a compound of Formulas (I) and/or (VI) according to the invention or a pharmaceutically acceptable salt or stereosomer thereof.

For preparing a medicament from a compounds of Formulas (I) and/or (VI), pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify. Compositions suitable for vaginal administration may be presented as pessaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The compounds of Formulas (I) and/or (VI) according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

In one embodiment of the present invention, the medicament is applied topically or systemically or via a combination of the two routes.

In an especially preferred embodiment of the present invention the medicament is applied topically. This reduces possible side effects and limits the necessary treatment to those areas affected.

In another especially preferred embodiment of the present invention the medicament is applied systemically.

Preferably the medicament is prepared in form of an ointment, a gel, a plaster, an emulsion, a lotion, a foam, a cream of a mixed phase or amphiphilic emulsion system (oil/water-water/oil mixed phase), a liposome, a transfersome, a paste or a powder.

Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co. Easton, Pa.).

Pharmaceutical compositions can also contain two or more compounds of the Formulas (I) and/or (VI) or their pharmacologically acceptable salts and also other therapeutically active substances.

Thus, the compounds of the present invention can be used in the form of one compound alone or in combination with other active compounds—for example with medicaments already known for the treatment of the aforementioned diseases, whereby in the latter case a favorable additive, amplifying effect is noticed. Suitable amounts to be administered to humans range from 0.5 to 500 mg.

To prepare the pharmaceutical preparations, pharmaceutically inert inorganic or organic excipients can be used. To prepare pills, tablets, coated tablets and hard gelatin capsules, for example, lactose, corn starch or derivatives thereof, talc, stearic acid or its salts, etc. can be used. Excipients for soft gelatin capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

In general, a daily dose of approximately 0.1 mg to 500 mg, preferably 1 to 50 mg, per human individual is appropriate in the case of the oral administration. In the case of other administration forms too, the daily dose is in similar ranges. For topical delivery, depending on the permeability of the skin, the type and the severity of the disease and dependent on the type of formulation and frequency of application, different concentrations of active compounds within the medicament can be sufficient to elicit a therapeutic effect by topical application. Preferably the concentration of an active compound or a pharmaceutically acceptable salt thereof or a stereoisomer thereof within a medicament according to the invention is in the range of between 1 µmol/ and 100 mmol/l.

The following examples and figures are included to demonstrate preferred embodiments of the invention. It should be appreciated by those of skill in the art that the techniques disclosed in the examples that follow represent techniques discovered by the inventors to function well in the practice of the invention, and thus can be considered preferred modes for its practice.

EXAMPLES

Abbreviations: min, minute(s); h, hour(s); r.t., room temperature, Phe, Phenylalanin, Trp, Tryptophan, TBTU, O-Benzotriazol-1-yl-N,N,N',N'-tetramethyluronium tetrafluoroborate, 2-Nal, L-2-Naphtylalanin, Z, Benzyloxycarbonyl.

NMR spectra: Bruker Avance 300 MHz. The spectra were recorded at 305 K and 300.13 MHz ($^1$H-NMR), respectively, using the residual solvent peak as an internal standard (DMSO-$d_6$, $\delta_H$=2.49; CD$_3$OD, $\delta_H$=3.31; CDCl$_3$, $\delta_H$=7.26; CD$_3$CN, $\delta_H$=1.93; (CD$_3$)$_2$CO, $\delta_H$=2.05).

Analytical LC/ESI-MS: 2× Waters 600 Multisolvent Delivery System. 50 µl sample loop. Column, Chromolith Speed ROD RP18e (Merck, Darmstadt), 50×4.6 mm, with 2 µm prefilter (Merck). Eluent A, H$_2$O+0.1% HCO$_2$H; eluent B, MeCN. Gradient, 5% B to 100% B within 5 min; flow, 3 ml/min. Waters LCZ single quadrupol mass spectrometer with electrospray source. MS method, MS8minPM-80-800-20V; positive/negative ion mode scanning, m/z 80-800 in 1 s; capillary, 3.5 kV; cone voltage, 20 V; multiplier voltage, 400 V; probe and desolvation gas temperature, 120° C. and 350° C., respectively. Waters 2487 Dual λ Absorbance Detector, set to 254 nm.

Preparative HPLC-MS: Waters 600 Multisolvent Delivery System with peparative pump heads. 2000 µl or 5000 µl sample loop. Column, Waters X-Terra RP18, 7 µm, 19×150 mm with X-Terra RP18 guard cartridge 7 µm, 19×10 mm; used at flow rate 20 ml/min or YMC ODS-A, 120 Å, 40×150 mm with X-Terra RP18 guard cartridge 7 µm, 19×10 mm; used at flow rate 50 ml/min. Make-up solvent: MeCN—$H_2O$—$HCO_2H$ 80:20:0.05 (v:v:v). Eluent A, $H_2O$+0.1% $HCO_2H$; eluent B, MeCN. Different linear gradients from 5-100% eluent B, adapted to sample. Injection volume: 500 µl-2000 µl depending on sample. Waters ZQ single quadrupol mass spectrometer with electrospray source. Positive or negative ion mode scanning m/z 80-800 in 1 s; capillary, 3.5 kV or 3.0 kV; cone voltage, 20 V; multiplier voltage, 400 V; probe and desolvation gas temperature, 120° C. and 350° C., respectively.

Waters Fraction Collector II with mass-triggered fraction collection. Waters 996 photo diode array detector.

Synthesis of Phe-Aminohydantoin

Boc-Phe-Aldehyd (2 mmol), Aminohydantoin (2 mmol) and Sodiumacetate (4 mmol) were dissolved in 20 ml ethanol/water (1:1). The mixture was refluxed for 4 hours. After cooling to room temperature the solid product (Boc-Phe-Aminohydantoin) was filtered and dried in vaccuo.

The resulting Boc-Phe-Aminohydantoin (0.25 mmol) was dissolved in 5 ml 4M HCl/Dioxan. The solution was stirred for 2 hours at room temperature. Afterwards the solvent was removed and the residue was washed with diethyl ether. Solid product was dried in vaccuo.

Alternative Synthesis of (1-[(2,4-Dioxo-imidazolidin-1-ylimino)-methyl]-2-phenyl-ethyl}-carbamic acid tertbutylester Boc-L-Phe-Aldehyd ( was obtained from Bachem AG, Hauptstrasse 144, 4416 Bubendorf-Switzerland) (2 mmol, Aminohydantoin (2 mmol) were dissolved in 50 ml Trimethylorthoformate and 2 mmol diisopropylethylamine. The mixture was stirred at room temperature for 48 hours. The solvent was removed in the vacuum, water added to the oily residue. The residue becomes solid after standind in the cold. The solid product was filtered and dried in vaccuum.

1-(2-Amino-3-phenyl-propylideneamino)-imidazolidine-2,4-dione

{1-[(2,4-Dioxo-imidazolidin-1-ylimino)-methyl]-2-phenyl-ethyl}-carbamic acid tert-butyl ester (0.25 mmol) was dissolved in 5 ml 4M HCl/Dioxan (other concentrations of HCl and different reaction times cam be employed to remove the Boc group. Also, trifluoroacetic acid at various concentrations can be employed to remove the BOC group. The solution was stirred for 2 hours at room temperature. Afterwards the solvent was removed and the residue was washed with diethyl ether. Solid product was dried in vaccuo.

Compound 1

Z-Trp-Trp-OH (0.1 mmol), 1-Hydroxybenzotriazolhydrate (0.1 mmol), and TBTU (0.1 mmol) were dissolved in dry dimethylformamide and stirred at r.t. After a few minutes Phe-Aminohydantoin (0.11 mmol) solved in dimethylformamide was added in portions and the reaction was allowed to reach room temperature over 18 hours. The solvent was removed and the residue was redissolved in ethyl acetate. The solution was washed with 1 mol/l HCl, and with 10% $Na_2CO_3$ and then dried over $MgSO_4$. The reaction was filtered and the solvent was removed in vaccuo. The compound was purified by preparative HPLC.

Alternative Synthesis of Compound 1 tert-Butyl 1-(methoxy(methyl)amino)-1-oxo-3-phenylpropan-2-ylcarbamat (a)

10.00 g (37.69 mmol) N-t-BOC-L-phenylalanin, 4.87 g (37.69 mmol) N,N-diisopropylethylamin and 3.68 g (37.69 mmol) N,O-dimethylhydroxylamin-hydrochloride were dissolved in 50 ml N,N-dimethylformamid. The solution is cooled in an ice bath and 7.23 g (37.69 mmol) N-(3-dimethylaminopropyl)-N-ethylcarbodiimid-hydrochlorid is added in portions while stirring. Stirring is continued over night. The solvent is removed in the vacuum and the residue dissolved in ethylacetate. The organic phase is washed with saturated sodiumbicarbonate, 5% citric acid and water. The solution is dried with magnesiumsulfate, the solvent removed in the vacuum and the product dried in the high vacuum. Yield 10.00 g

2-Amino-N-methoxy-N-methyl-3-phenylpropanamid-Hydrochlorid (b)

10.00 g (32.43 mmol) a is dissolved in 100 ml 4M HCl in dioxan and stirred for 1 hour. The solvent is removed in the vacuum and the residue washed with ether on a filter, filtered and dried in the vacuum. Yield 8.85 g white solid.

(2-(1H-Indol-3-yl)-1-{2-(1H-indol-3-yl)-1-[1-(methoxy-methyl-carbamoyl)-2-phenyl-ethylcarbamoyl]-ethylcarbamoyl}-ethyl)-carbamic acid benzyl ester (c)

8.85 g (36.16 mmol) b, 18.97 g (36.16 mmol) Z-Trp-Trp-OH, 4.89 g (36.16 mmol) 1-hydroxybenzotriazo und 9.35 g (72.33 mmol) N,N-diisopropylethylamin were dissolved in 200 ml dry N,N-dimethylformamid. The solution is cooled in an ice bath and 15.09 g (39.78 mmol) O-benzotriazol-1-yl-N,N,N',N'-tetramethyluronium hexafluorophosphat is added in portions while stirring. The solution is stirred over night at room temperature. The solvent is removed in the vacuum, dissolved in ethylacetate and washed with saturated sodiumbicarbonate, 5% citric acid, dried with magnesiumsulfate and concentrated in the vacuum, to obtain 34.59 g crude product.

The crude product is purified by flash chromatography on silicagel using (Eluent: dichlormethane:methanol:conz. ammonia=90:10:1 as eluent. Yield 20 g

[1-[1-(1-Formyl-2-phenyl-ethylcarbamoyl)-2-(1H-indol-3-yl)-ethylcarbamoyl]-2-(1H-indol-3-yl)-ethyl]-carbamic acid benzyl ester (d)

1.00 g (1.40 mmol) (c) is dissolved in 10 ml dry THF and coole in an isopropanol/dry ice bath. To the solution 2 ml 1M lithiumaluminiumhydride in dry THF is added and the solution stirred for 1 to 2 hours. The reaction mixture is warmed up to room temperature and quenched with water. The water phase extracted with ethylacetate, the ethylacetate phase dried with magnesiumsulfate and concentrated in the vacuum. After driying in the high vacuum 1.03 g yellow foam is obtained. The product is used in the next step without further purification.

Compound 1

1.03 g (1.57 mmol) (d) is dissolved in a mixture of 5 ml trimethylorthoformate and 5 ml DMF. Then, 0.24 g (1.57 mmol) 1-aminohydantoin-hydrochloride and 0.20 g (1.57 mmol) N,N-diisopropylethylamine is added and the reaction mixture is stirred at room temperature for 48 hours. The solvent was removed in the vacuum and water added to the residue and a solid product is obtained. The solid product is the filtered and dried in the vacuum, to obtain 0.73 g crude product.

Purification by flash chromatography (eluent: dichlormethane:methanol=90:10) on silicagel yields 0.31 g pure product.

Compound 1 D-Phe-L-Trp-L-Z-Trp

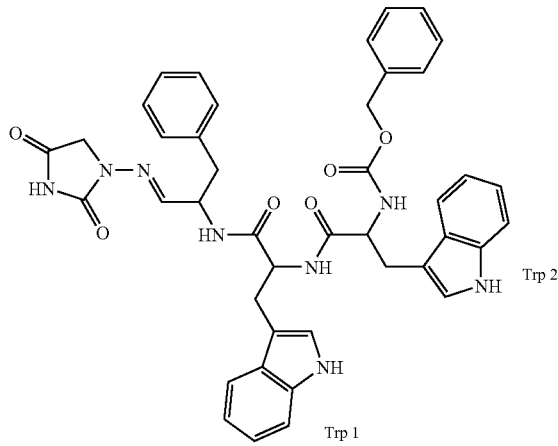

| Chemical shift | correlation | Number of protons | multiplicity (coupling constant) |
| --- | --- | --- | --- |
| 11.732 ppm | $NH_{Hyd}$ | 1H | |
| 10.7442 ppm | $H\epsilon_{Trp1}$ | 1H | d (4.2 Hz) |
| 10.7354 ppm | $H\epsilon_{Trp2}$ | 1H | d (4.5 Hz) |
| 8.3376 ppm | $NH_{Phe}$ | 1H | d (8.4 Hz) |
| 7.908 ppm | $NH_{Trp1}$ | 1H | d (8.3 Hz) |
| 7.5629 ppm | $H_{X2\ Trp2}$ | 1H | d (8.0 Hz) |
| 7.5332 ppm | $H_{X2\ Trp1}$ | 1H | d (7.6 Hz) |
| 7.326–6.916 ppm | $H_{arom}$ von Trp1, Trp2, Z, Phe $H_\delta$ von Trp1, Trp2 $NH_{Trp2}$ | 21H | m |
| 6.946 ppm | $H_{Hyd}$ | 1H | d (4.5 Hz) |
| 4.9181 ppm | $CH_{2\ Z}$ | 2H | m |
| 4.6868 ppm | $H\alpha_{Phe}$ | 1H | dddd (9.1 Hz - $H_\beta$, 5.9 Hz - $H_\beta$, 4.5 Hz - $H_{Hyd}$, 8.4 Hz - $NH_{Phe}$) |
| 4.541 ppm | $H\alpha_{Trp1}$ | 1H | m |
| 4.2583 ppm | $H\alpha_{Trp2}$ | 1H | m |
| 4.1014 ppm | $CH_{2\ Hyd}$ | 2H | s |
| 3.032-2.7229 ppm | $H_{\beta,\beta'}$ von Phe, Trp1, Trp2 | 6H | m |

| L-Isomer of Compound 1 - L-Phe-L-Trp-L-Z-Trp | | | |
| --- | --- | --- | --- |
| Chemical shift | correlation | Number of protons | multiplicity (coupling constant) |
| 11.1431 ppm | $NH_{Hyd}$ | 1H | |
| 10.7858 ppm | $H\epsilon_{Trp1}$ | 1H | d (1.9 Hz) |
| 10.7514 ppm | $H\epsilon_{Trp2}$ | 1H | d (2.1 Hz) |
| 8.1784 ppm | $NH_{Phe}$ | 1H | d (8.2 Hz) |
| 8.0274 ppm | $NH_{Trp1}$ | 1H | d (8.4 Hz) |
| 7.5982 ppm | $H_{X2\ Trp2}$ | 1H | d (7.4 Hz) |
| 7.5686 ppm | $H_{X2\ Trp1}$ | 1H | d (7.9 Hz) |
| 7.349–6.925 ppm | $H_{arom}$ von Trp1, Trp2, Z, Phe $H_\delta$ von Trp1, Trp2 $NH_{Trp2}$ | 19H | m |
| 6.7041 ppm | $H_{Hyd}$ | 1H | d (4.9 Hz) |
| 4.9344 ppm | $CH_{2\ Z}$ | 2H | m |
| 4.5686 ppm | $H\alpha_{Trp1}$ | 1H | m |
| 4.3093 ppm | $H\alpha_{Trp2}$ | 1H | m |
| 3.980 ppm | $CH_{2\ Hyd}$ | 2H | s |
| 3.137–2.778 ppm | $H_{\beta,\beta'}$ von Phe, Trp1, Trp2 | 6H | m |

Compound 2 and 3

Compound 1 (0.13 mmol) is dissolved in 5 ml methanol. 10 mg Pd/C was added and the reaction mixture stirred under hydrogenatmosphere for 3 hours. The catalyst was filtered an the solvent was removed under vaccuo. The residue and the appropriate carboxylic acid (0.1 mmol) were dissolved in 1 ml dry dimethylformamide. Hydroxybenzotriazole, TBTU and Diisopropylethylamine (0.1 mmol each) were added at 0° C. and stirred at room temperature for 12 hours. The solvent was removed and the residue was redissolved in ethyl acetate. The solution was washed with 1 mol/l HCl, and with 10% $Na_2CO_3$ and then dried over $MgSO_4$. After filtration and the solvent was removed in vaccuo. The compound was purified by preparative HPLC.

Compound 4

Compound 1 (0.13 mmol) is dissolved in 5 ml methanol. 10 mg Pd/C was added and the mixture stirred under hydrogenatmosphere for 3 hours. The catalyst was filtered an the solvent was removed under vaccuo. The residue and Carbonic acid 4-nitro-phenyl ester pyridin-3-ylmethyl ester (0.1 mmol) were dissolved in 1 ml dry DMF and Diisopropylethylamine (0.1 mmol) was added at 0° C. and stirring continued at room temperature for 12 hours. The solvent was removed and the residue was diluted with ethyl acetate. The solution was washed with 1 mol/l HCl, and with 10% $Na_2CO_3$ and then dried over $MgSO_4$. The reaction was filtered and the solvent was removed in vaccuo. The compound was purified by preparative HPLC.

Compound 5

Z-pBromPhe-2-Nal-OH (0.1 mmol), 1-Hydroxybenzotriazolhydrate (0.1 mmol), and TBTU (0.1 mmol) were dissolved in dimethylformamide and stirred at r.t. After a few minutes Phe-Aminohydantoin (0.11 mmol) solved in dimethylformamide and Diisopropylethylamine (0.1 mmol) was added in portions and the reaction was stirred at room temperature over 18 hours. The solvent was removed and the residue was diluted with ethyl acetate. The solution was washed with 1 mol/l HCl, and with 10% $Na_2CO_3$ and then dried over $MgSO_4$. The reaction was filtered and the solvent was removed in vaccuo. The compound was purified by preparative HPLC.

Compound 6

Compound 5 (0.13 mmol) is dissolved in 5 ml methanol. 10 mg Pd/C was added and the mixture stirred under hydrogen-atmosphere for 3 hours. The catalyst was filtered an the solvent was removed under vaccuo. The residue and Carbonic acid 4-nitro-phenyl ester pyridin-3-ylmethyl ester (0.1 mmol) were dissolved in 1 ml dry Dimethylformamide and Diisopropylethylamine (0.1 mmol) was added at 0° C. and stirring continued at room temperature for 12 hours. The solvent was removed and the residue was diluted with ethyl acetate. The solution was washed with 1 mol/l HCl, and with 10% $Na_2CO_3$ and then dried over $MgSO_4$. The reaction was filtered and the solvent was removed in vaccuo. The compound was purified by preparative HPLC.

Examplary compounds of Formulas (I) and/or (VI) (1-9) and of formula (VI) (10-16) of the present invention include, but are not limited to, the followings:

| Cpd | Structure | human Proteasome $IC_{50}$ | $[M + H]^+$ |
|---|---|---|---|
| 1 | 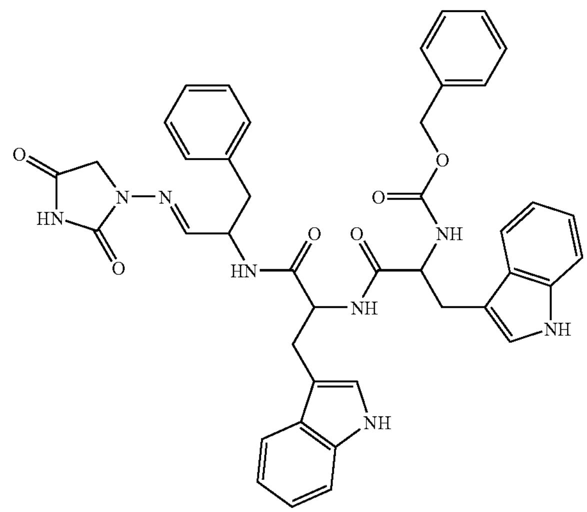 | 157 nm | 753 |
| 2 | 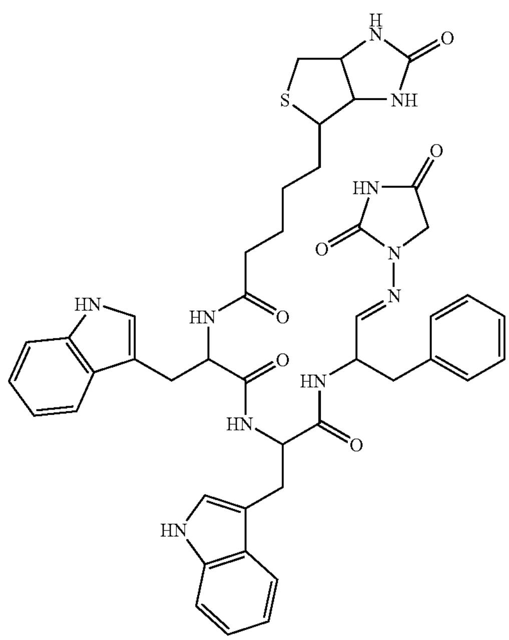 | 76 nM | 845 |

-continued

| Cpd | Structure | human Proteasome IC$_{50}$ | [M + H]$^+$ |
|---|---|---|---|
| 3 | 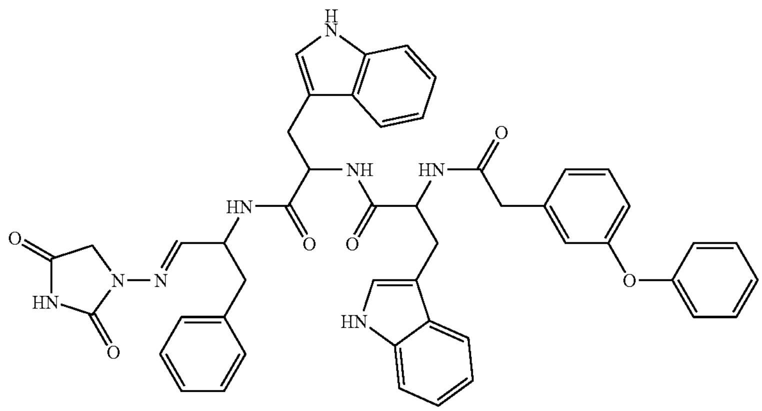 | 224 nm | 829 |
| 4 | 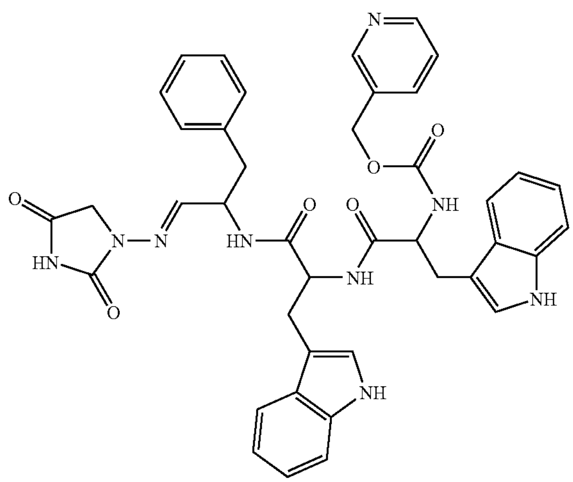 | 61 nm | 754 |
| 5 | 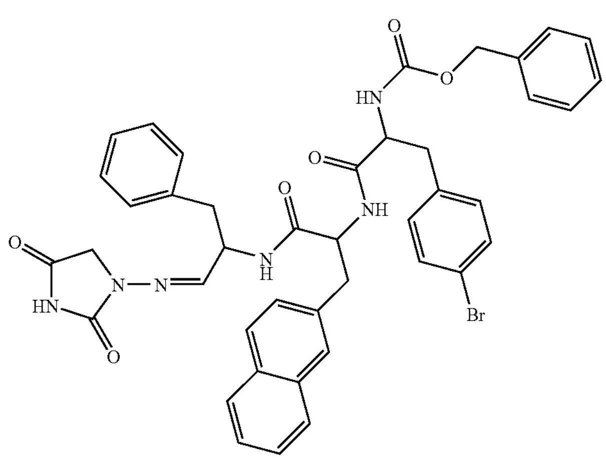 | nanomolar | 804 |

-continued

| Cpd | Structure | human Proteasome IC$_{50}$ | [M + H]$^+$ |
|---|---|---|---|
| 6 | 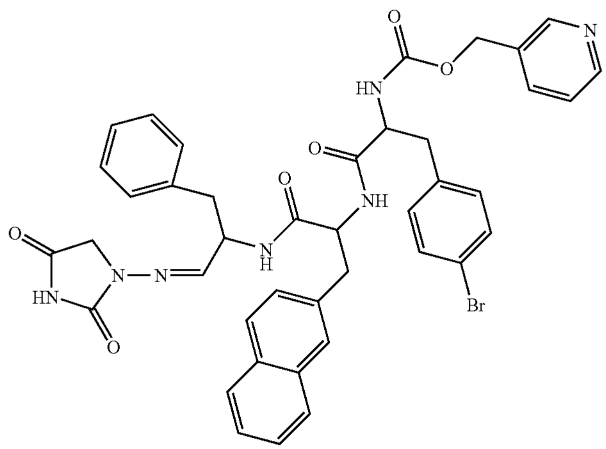 | nanomolar | 805 |
| 7 | 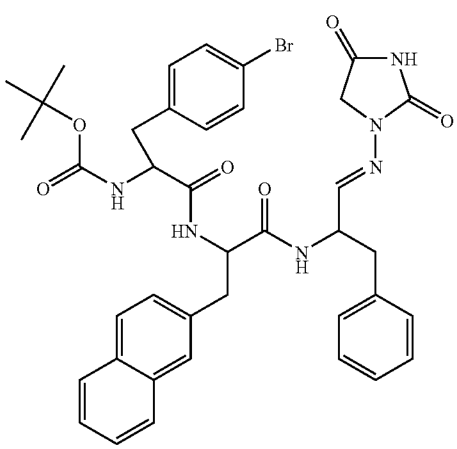 | nanomolar | Not measured |
| 8 | 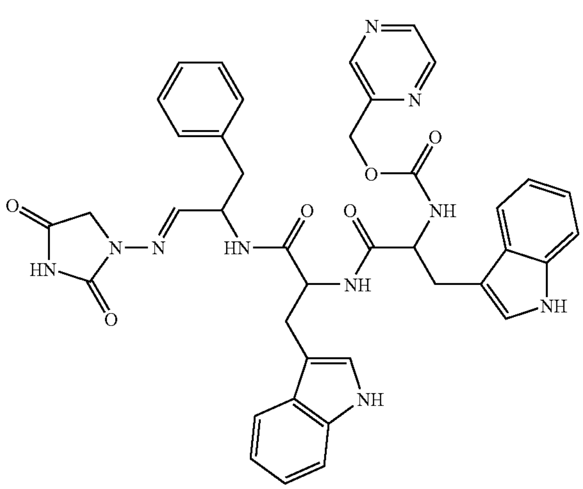 | 133 nm | Not measured |

| Cpd | Structure | human Proteasome IC$_{50}$ | [M + H]$^+$ |
|---|---|---|---|
| 9 | 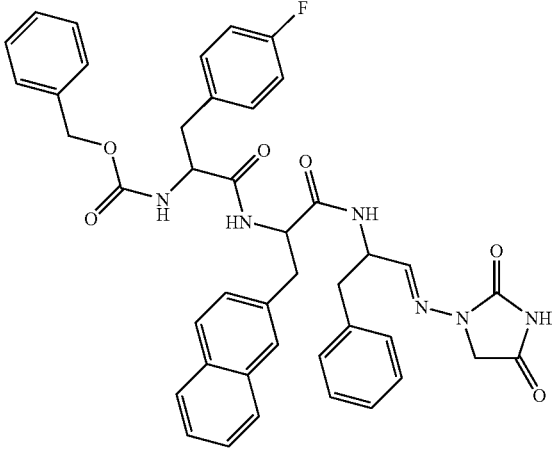 | nanomolar | Not measured |
| 10 | 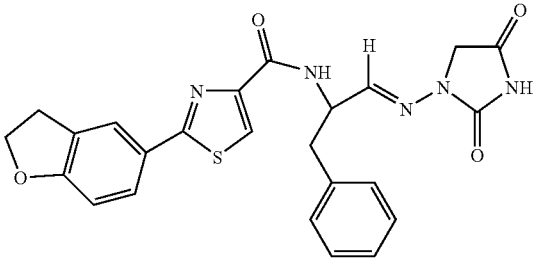 | 3.5 μm | 476 |
| 11 | 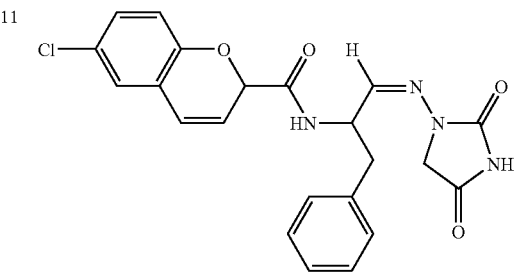 | 3.54 μm | 439 |
| 12 | 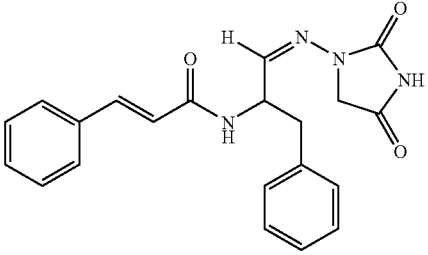 | 2.21 μm | 377 |

-continued

| Cpd | Structure | human Proteasome IC$_{50}$ | [M + H]$^+$ |
|---|---|---|---|
| 13 | 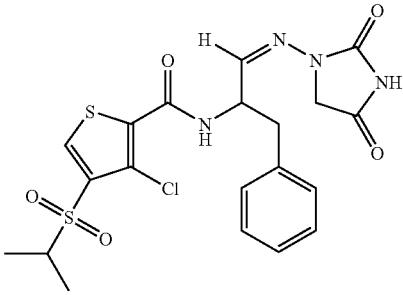 | Not measured | 497 |
| 14 | 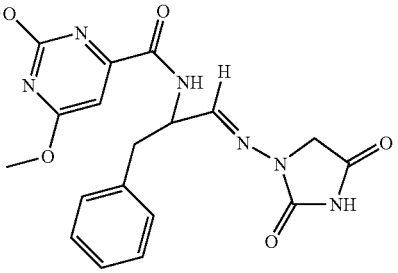 | 2.96 μm | 413 |
| 15 | 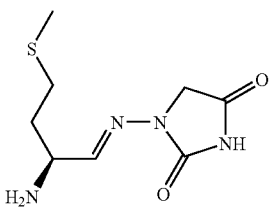 | Not measured | Not measured |
| 16 | 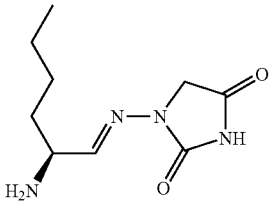 | Not measured | Not measured |
| 17 | 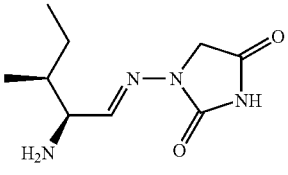 | Not measured | Not measured |

Biological Activity:

The chymotryptic activity of the 20S proteasome (Immatics, Tübingen) was determined using a Tecan Ultra plate reader and Suc-LLVT-AMC as substrate (Bachem). In the wells of a black 96 well polypropylene plate, 2 μl of the respective inhibitor dissolved in DMSO were mixed with 50 μl substrate solution (25 mM HEPES pH 7.5 at 20° C., 0.5 mM EDTA and Suc-LLVT-AMC (in the appropriate concentration) and the reaction was initiated by adding 150 μl proteasome solution (1.3 μg/ml 20S proteasome in 25 mM HEPES pH 7.5 at 20° C., 0.5 mM EDTA, 0.033% (w/v) SDS). Substrate hydrolysis was followed by fluorescence spectroscopy (excitation wavelength: 360 nm; emission wavelength: 465 nm) for 20 min at 30° C. and initial velocities were calculated and expressed as change in relative fluorescence units (RFU) per second.

The activity of cathepsin S (Biomol) was determined using a Tecan Ultra plate reader and Z-Val-Arg-Arg-AMC as substrate (Bachem). In the wells of a black 96 well polypropylene plate, 1 μl of the respective inhibitor dissolved in DMSO was mixed with 90 μl enzyme solution (0.09 nM cathepsin S in 25 mM HEPES, pH 7.4, 100 mM NaCl, 1 mM DTT). The reaction was started by addition of 10 μl substrate (400 μM in 25 mM HEPES, pH 7.4, 100 mM NaCl, 1 mM DTT). Substrate hydrolysis was followed by fluorescence spectroscopy (excitation wavelength: 360 nm; emission wavelength: 465 nm)

for 10 min at room temperature (22° C.) and initial velocities were calculated and expressed as change in relative fluorescence units (RFU) per second. Active compounds showed an inhibition of 200 nM to 10 µM.

Influence of compounds according to the invention on keratinocyte proliferation.

Individual wells of a 96-well tissue-culture microtiter plate (Greiner) were inoculated with 100 µl medium containing 14000 cells. The medium was Earle's MEM+10% FCS (complete medium). The plates were incubated for 24 hours to enable cellular attachment. Thereafter, the medium was removed and the cells were re-fed with 100 µl treatment medium containing different concentrations of the compounds, negative (cell culture with culture medium (Earle's MEM with 10% FCS)) and positive control extracts (3.13-250 µg/ml SDS in Earle's MEM with 10% FCS and 10% deionized water), and solvent control (cell culture with culture medium (Earl's MEM with 10% FCS) and 1% (v/v) DMSO for compounds or 10% (v/v) deionized water for SDS), respectively. The test compounds were dissolved in DMSO and then further diluted in culture medium with a final concentration of 1% DMSO All incubations were done at 37° C. in a humified atmosphere with 5% $CO_2$. After an incubation period of 24 hours, 50 µl of the XTT labelling mixture was added to each well. This mixture consists of the XTT labelling reagent (5 ml) and of the electron coupling reagent (100 µl). The cells were incubated for approximately 1 hour and 40 minutes and subsequently transferred to a microplate reader equipped with a 450 nm filter to read the absorbance. Compounds showed an inhibition of keratinocyte proliferation at concentrations below 50 µM.

Thus, the compounds of formula I are suitable for treating skin diseases or skin diseases associated with abnomal cell proliferation.

Inhibition of stimulated peripheral blood monocytes (PBMC). PBMCs were isolated from the blood of healthy volunteers with the help of ACCUSPIN™ System HISTO-PAQUE®-1077 tubes, washed and resuspended with $10.\sup 6$ cells/ml in Dulbecco's modified eagles medium, containing 10% fetal calf serum and 2 mM Glutamine.

The cells were stimulated with 2 µg/ml phytohemoagglutinin in the presence of test compound or blank vehicle for 72 h. 4 h prior to the end of the incubation period, 5-bromo-2'-desoxyuridine (BrdU) was added to label the proliferating cells. After the incubation, the cells were separated by centrifugation and the culture supernatant removed. Incorporated BrdU was quantified with the help of an enzyme-linked immunosorbent assay.

For the determination of the $IC_{50}$ values (concentration of inhibitor required for 50% inhibition) at least four different inhibitor concentrations were applied. Each data point was recorded in triplicates. Curves were fitted with the a suitable program. Compounds showed an inhibition of PBMC proliferation at concentrations below 50 µM.

Thus, the compounds of Formulas (I) and/or (VI) are suitable for treating inflammatory diseases or diseases associated with T cells.

Inhibition of U266 Cells proliferation (multiple myeloma)

For the determination of the anti-proliferation/cytotoxic activity of the compounds, U 266 cells (humane multiple myeloma cells) were used.

The cells were plated to approximately 50 000-100 000 cells/well in a sterile 96-well flat bottom Multiplate (Corning, Netherlands). The Incubation at 37.degree. C., 5% $CO_2$ 90% relative humidity was made in the presence of different concentrations of the compound. All cells were incubated for 72 hours over a concentration range of 0.05-100 µM using one of the compounds (1-6) described before with a final volume of 100 µl per well. After incubation, a MTS assay (10 µM CELL-TITER 96®. $AQ_{uerous}$ One Solution (Promega U.S.A.). was added and incubated for 2 hrs) was used to determinate the number of viable cells. The culture medium employed was RPMI 1640 which contained 10% heat inactivated fetal bovine serum, 100 units/ml penicillinG and 100 µg/ml streptamycin sulfate. The reaction product was quantified by measuring the absorbance at the respective wavelength using an ELISA reader. The EC50 values were determined using a fitting function. Compounds inhibited the proliferation at a concentration below 20 micromolar.

Thus, the compounds of Formulas (I) and/or (VI) are suitable for treating multiple myeloma.

What is claimed is:

1. A compound of formula (V):

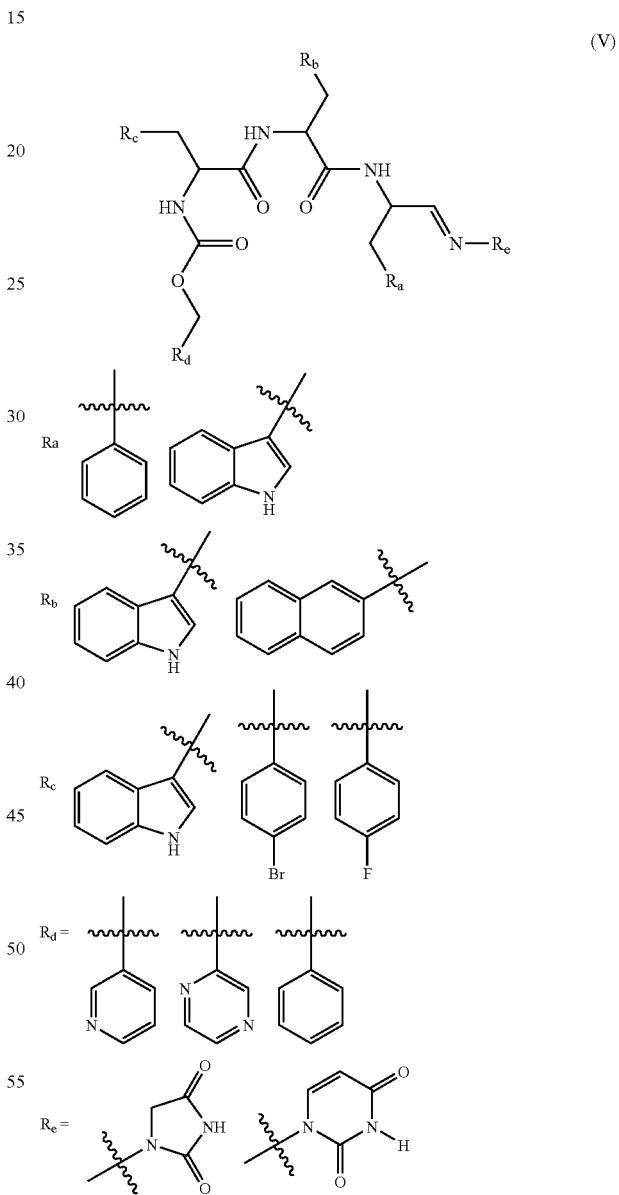

and wherein $R_a$, $R_b$, $R_c$, $R_d$, and $R_e$ are selected independently from each other.

2. The compound of formula (V) according to claim 1, wherein the configuration of the chiral centers is "S".

* * * * *